US011071927B2

(12) United States Patent
Kushnir et al.

(10) Patent No.: US 11,071,927 B2
(45) Date of Patent: Jul. 27, 2021

(54) SEPARATING AND QUANTIFYING UNBOUND TARGET ANALYTES FROM BIOLOGICAL SAMPLES

(71) Applicant: ARUP Laboratories, Inc, Salt Lake City, UT (US)

(72) Inventors: Mark M. Kushnir, Salt Lake City, UT (US); Alan L. Rockwood, Riverton, UT (US)

(73) Assignee: ARUP Laboratories, Inc., Salt Lake City, UT (US)

( * ) Notice: Subject to any disclaimer, the term of this patent is extended or adjusted under 35 U.S.C. 154(b) by 324 days.

(21) Appl. No.: 15/929,064

(22) Filed: Nov. 15, 2018

(65) Prior Publication Data
US 2019/0329153 A1 Oct. 31, 2019

Related U.S. Application Data

(60) Provisional application No. 62/586,798, filed on Nov. 15, 2017.

(51) Int. Cl.
*B01D 15/34* (2006.01)
*G01N 33/538* (2006.01)
(Continued)

(52) U.S. Cl.
CPC ............. *B01D 15/34* (2013.01); *C07K 1/16* (2013.01); *G01N 33/538* (2013.01); *G01N 33/74* (2013.01); *G01N 33/82* (2013.01)

(58) Field of Classification Search
CPC ........ B01D 15/34; C07K 1/16; G01N 33/538; G01N 33/74; G01N 33/82
See application file for complete search history.

(56) References Cited

U.S. PATENT DOCUMENTS 4,456,689 A 6/1984 Witty et al.
5,527,902 A * 6/1996 Loth ................. B01J 20/24
428/402
(Continued)

FOREIGN PATENT DOCUMENTS

WO WO-2006015796 A1 * 2/2006 ........... G01N 33/538

OTHER PUBLICATIONS

Bikle et al.; "Free 25-Hydroxyvitamin D Levels are normal in Subjects with Liver Disease and Reduced Total 25-Hydroxyvitamin D Levels;" The Journal of Clinical Investigation; (Sep. 1986); pp. 748-752; vol. 78, No. 3; <doi: 10.1172/JCI112636 >.
(Continued)

*Primary Examiner* — Jennifer Wecker
(74) *Attorney, Agent, or Firm* — Todd Alder

(57) ABSTRACT

A method of separating free target analyte from protein-bound target analyte is described. Such can include obtaining an aqueous sample containing a target analyte in a free form (free target analyte) and the target analyte in a protein-bound form (protein-bound target analyte), passing the aqueous sample through a size exclusion chromatography matrix with a molecular weight cut off sufficient to allow the free target analyte to permeate into pores of the size exclusion chromatography matrix and exclude the protein-bound target analyte, whereupon the free target analyte adheres to and is immobilized by the size exclusion chromatography matrix and the protein-bound target analyte does not adhere to by the size exclusion chromatography matrix, separating the free target analyte from the protein-bound analyte by removing the protein-bound target analyte from the size exclusion chromatography matrix, and eluting the free target analyte from the size exclusion chromatography matrix with an organic solvent.

20 Claims, 1 Drawing Sheet

(51) Int. Cl.
G01N 33/82 (2006.01)
G01N 33/74 (2006.01)
C07K 1/16 (2006.01)

(56) References Cited

U.S. PATENT DOCUMENTS

| | | | |
|---|---|---|---|
| 7,179,592 | B2 | 2/2007 | Dunayevskiy et al. |
| 8,617,898 | B2 | 12/2013 | Dey et al. |
| 8,987,002 | B2 | 3/2015 | Singh et al. |
| 9,188,596 | B2 | 11/2015 | Dey et al. |
| 9,606,131 | B2 | 3/2017 | Thadhani et al. |
| 9,897,615 | B2 | 2/2018 | Martens et al. |
| 2002/0052006 | A1* | 5/2002 | Dunayevskiy ..... G01N 33/6845 435/7.1 |
| 2006/0240633 | A1* | 10/2006 | Martosella ............... C07K 1/16 438/348 |
| 2013/0197200 | A1* | 8/2013 | Bian .................... B01D 15/363 530/388.1 |
| 2015/0247872 | A1* | 9/2015 | Thadhani ............. A61K 31/593 514/167 |

OTHER PUBLICATIONS

Bikle et al.; "Assessment of the Free Fraction of 25-Hydroxyvitamin D in Serum and Its Regulation by Albumin and the Vitamin D-Binding Protein;" Journal of Clinical Endocrinology and Metabolism; (Oct. 1986); pp. 954-959; vol. 63, No. 4; <doi: 10.1210/jcem-63-4-954 >.

Bikle et al.; "Vitamin D Metabolites in Captivity? Should we Measure Free or Total 25(OH)D to Assess Vitamin D Status?," Journal of Steroid Biochemistry & Molecular Biology; (Oct. 1, 2017); pp. 105-116; vol. 173; <doi: 10.1016/jjsbmb.2017.01.007 >.

Hedman et al.; "Development of a Sensitive LC/MS/MS Method for Vitamin D Metabolites: 1,25. Dihydroxyvitamin $D_2$&$_3$ Measurement Using a Novel Derivatization Agent;" Journal of Chromatography B: Analytical Technologies in the Biomedical and Life Sciences; (Mar. 15, 2014); pp. 62-67; <doi: 10.1016/j.jchromb.2014.01.045 >.

Henderson et al.; "Measurement by a Novel LC-MS/MS Methodology Reveals Similar Serum Concentrations of Vitamin D-Binding Protein in Blacks and Whites;" Clinical Chemistry; (2016); pp. 179-187; vol. 62, No. 1; <doi: 10.1373/clinchem.2015.244541 >.

Higashi et al.; "Application of Cookson-Type Reagents for Biomedical HPLC and LC/MS Analyses: A Brief Overview;" Biomedical Chromatography; (Aug. 2016); 10 pages; vol. 31: e3808; <doi: 10.1022/bmc.3808 >.

Hollis et al.; "Vitamin D-Binding Protein and Vitamin D in Blacks and Whites;" New England Journal of Medicine; (Feb. 27, 2014); pp. 879-880; vol. 370, No. 9; <doi: 10.1056/NEJMc1315850# SA4 >.

Hoofnagle et al.; "Vitamin D-Binding Protein Concentrations Quantified by Mass Spectrometry;" New England Journal of Medicine; (Oct. 8, 2015); pp. 1480-1482; vol. 373, No. 15; <doi: 10.1056/ NEJMc1502602 >.

Hoofnagle; "Why Should We Use Mass Spectrometry to Measure Vitamin D Metabolites?;" [PowerPoint]; University of Washington VDSP; (Nov. 15, 2013); 51 pages.

Kota et al.; "Improving Proteome Coverage by Reducing Sample Complexity via Chromatography;" Chapter 5, Section 5.4, Size Exclusion Chromatography; Modern Proteomics—Sample Preparation, Analysis and Practical Applications, Advances in Experimental Medicine and Biology; (2016); pp. 83-143; vol. 919; <doi: 10.1007/978-3-319-41448-5_5 >.

Malmstoem et al.; "Current Assays to Determine Free 25-Hydroxyvitamin D in Serum;" Journal of AOAC International; (2017); pp. 1323-1327; vol. 100, No. 5; <doi: 10.5740/jaoacint.17-0085 >.

Mendel; "The Free Hormone Hypothesis Distinction from the Free Hormone Transport Hypothesis;" Journal of Andrology; (Mar./Apr. 1992); pp. 107-116; vol. 13, No. 2.

Mendel; "The Free Hormone Hypothesis: A Physiologically Based Mathematical Model;" Endocrine Reviews; (Aug. 1989); pp. 232-374; vol. 10, No. 3.

Müller et al.; "Mass Spectrometric Profiling of Vitamin D Metabolites Beyond 25-Hydroxyvitamin D;" Clinical Chemistry; (Mar. 2015); pp. 1033-1048; vol. 61, No. 8; <doi: 10.1373/clinchem.2015. 241430 >.

Nielson et al.; "Role of Assay Type in Determining Free 25-Hydroxyvitamin D Levels in Diverse Populations;" New England Journal of Medicine; (Apr. 28, 2016); pp. 1695-1696; vol. 374, No. 17; <doi: 10.1056/NEJMc1513502 >.

Answer ID: E12864; "Zeba™ Product FAQS—E12864 Documents & Support;" Thermo Fisher Scientific; (Upon Knowledge and Belief Prior to Nov. 4, 2018); 1 page; [retrieved on Mar. 18, 2019]; Retrieved from <URL: https://www.thermofisher.com/search/results? query=E12864&focusarea=Search%20All >.

Bouillon et al.; "Influence of the Vitamin D-Binding Protein on the Serum Concentration of 1.25- Dihydroxyvitamin Ds;" The Journal of Clinical Investigation; (Mar. 1981); pp. 589-596. vol. 67, Issue 3.

Vermeulen et al.; "A Critical Evaluation of Simple Methods for the Estimation of Free Testosterone in Serum;" The Journal of Clinical Endocrinology & Metabolism; (1999); pp. 3666-3672; vol. 84, No. 10.

* cited by examiner

SEPARATING AND QUANTIFYING UNBOUND TARGET ANALYTES FROM BIOLOGICAL SAMPLES

CROSS REFERENCE TO RELATED APPLICATION

This application claims the benefit of U.S. Provisional Patent Application Ser. No. 62/586,798, filed Nov. 15, 2017, which is incorporated herein by reference.

TECHNICAL FIELD

The present disclosure provides methods of separating and quantifying "free" (i.e., non-protein-bound) target analytes from biological fluid samples in which these target analytes exist in both free and protein-bound states. Also provided are kits and compositions related to the disclosed methods.

BACKGROUND

Biological fluid samples are complex mixtures containing a multitude of different components. Often there is a need to separate and quantify specific individual molecular components (i.e., analytes), or classes of components (i.e., related analytes), which are present in such biological fluid samples in very low concentrations. Such components can include various types of biologically active "small molecules," including steroids, secosteroids, phytosteroids, and certain drugs, and their metabolites. In many instances, these small molecule components exist in both free (i.e., non-protein-bound) and protein-bound states, sometimes being tightly bound by specific binding proteins, and sometime loosely bound or associated with other, more abundant, proteins, such as, for example serum albumin.

For example, certain steroids, secosteroids, phytosteroids, certain drugs, or their metabolites, are found in human plasma either tightly bound by specific binding-proteins, or loosely bound by abundant serum proteins, such as albumin, or both. However, a small fraction of such steroids, secosteroids, phytosteroids, drugs, or their metabolites, also exist in an unbound, or non-protein-bound, "free" state.

BRIEF DESCRIPTION OF THE DRAWINGS

The present disclosed teachings will be more fully understood with reference to the drawings provided. These drawings are intended to illustrate, but not to limit, the present disclosed teachings.

DETAILED DESCRIPTION

Figure 1A:
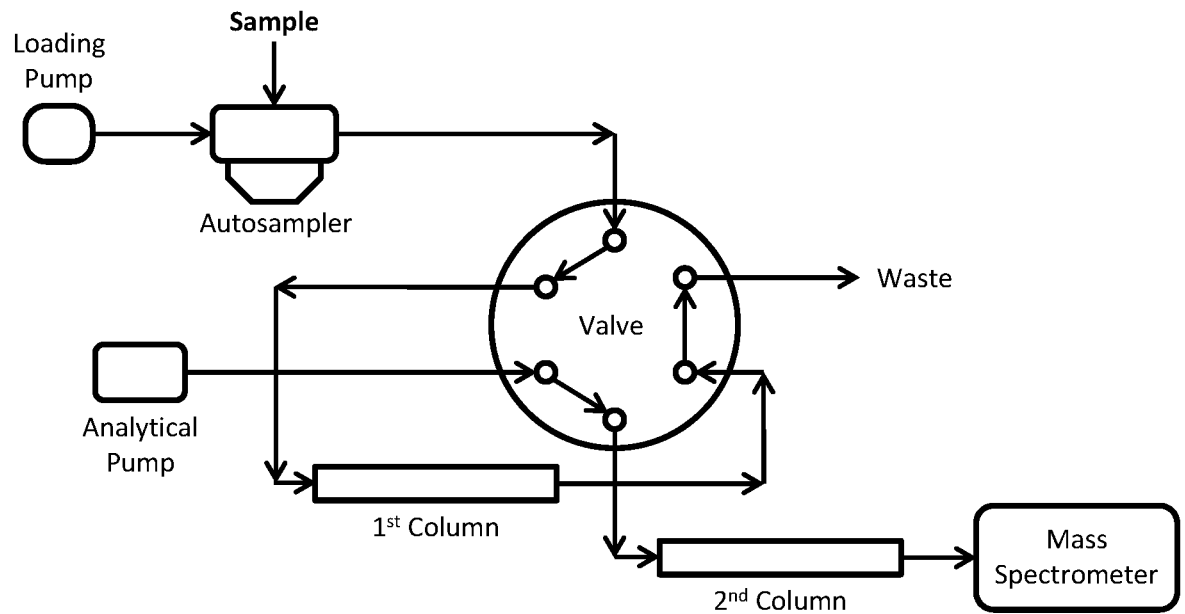
FIG. 1A schematically depicts one example setup for a chromatographic separation and detection method that can be employed in Examples 1 and 2, with the switching valve configured for loading a sample according to one example embodiment.

Although the following detailed description contains many specifics for the purpose of illustration, a person of ordinary skill in the art will appreciate that many variations, alterations, substitutions, and the like, to the following details can be made, and are considered to be included herein. Accordingly, the following embodiments are set forth without any loss of generality to, and without imposing limitations upon, any claims set forth. It is also to be understood that the terminology used herein is for describing particular embodiments only, and is not intended to be limiting. Unless defined otherwise, all technical and scientific terms used herein have the same meaning as commonly understood by one of ordinary skill in the art to which this disclosure belongs. Also, the same reference numerals in appearing in different drawings represent the same element. Numbers provided in flow charts and processes are provided for clarity in illustrating steps and operations and do not necessarily indicate a particular order or sequence.

Furthermore, the described features, structures, elements, characteristics, and the like, can be combined in any suitable manner in one or more embodiments. In the following description, numerous specific details are included to provide a thorough understanding of various embodiments. One skilled in the relevant art will recognize, however, that such detailed embodiments do not limit the overall concepts articulated herein, but are merely representative thereof. One skilled in the relevant art will also recognize that the technology can be practiced without one or more of the specific details, or with other methods, components, techniques, etc. In other instances, well-known structures, materials, operations, processes, or the like, may not be shown or described in detail to avoid obscuring aspects of the disclosure.

Particular advantages of the disclosed methods will be set forth in part in the description which follows, and in part will be apparent from the description, or may be learned by practice of specific embodiments of various methods. The advantages of the present technology will be realized and attained by use of various teachings disclosed herein. It is to be understood that both the foregoing general description and the following detailed description are exemplary and explanatory only, and are not restrictive.

For the purposes of this description, numerical or other ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. Further, it is to be understood that even when the term "about" is used in the present specification in connection with a specific numerical value, that support for the exact numerical value recited apart from the "about" terminology is also provided.

As used herein, a plurality of items, compositional elements, ingredients, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group, without indications to the contrary.

Concentrations, amounts, levels, solubility, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

For the purposes of this disclosure, the term "a" or "an" entity refers to one or more of that entity; for example, "a protein" refers to one or more proteins or at least one protein. As such, the terms "a" or "an," "one or more" and "at least one" can be used interchangeably herein. Furthermore, an element or means "selected from the group consisting of" or "comprising one or more of" refers to one or more of the elements in the list that follows, including mixtures (i.e. combinations) of two or more of the elements.

In this application, "comprises," "comprising," "containing" and "having" and the like can have the meaning ascribed to them in U.S. Patent law, and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

The terms "first," "second," "third," "fourth," and the like in the description and in the claims, if any, are used for distinguishing between similar elements, and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "worse," "higher," "lower," "enhanced," and the like, refer to a property of a composition, component, or activity that is measurably different from other compositions, components, or activities in a surrounding or adjacent area or environment, in a single composition or in multiple comparable compositions, in a group or class, in multiple groups or classes, or as compared to the known state of the art.

As used herein, the terms "analyte" or "target analyte" can be used interchangeably and mean a substance that is the subject of an analytical analysis, wherein this analytical analysis is intended to confirm the presence of, and in some examples quantify the amount or concentration of, the analyte in a biological sample.

The term "assay," as used herein, refers to any procedure, technique, method, or the like, for assessing the presence, amount, status or physical state of an analyte or multiple analytes. For example, in one embodiment, the analyte may be 25-hydroxy vitamin D3. In another embodiment, the analytes may be 25-hydroxy vitamin D3 and 25-hydroxy vitamin D2. In still another embodiment, the analytes may be 25-hydroxy vitamin D3, 25-hydroxy vitamin D2, 1,25-dihydroxy vitamin D3 and 1,25-dihydroxy vitamin D2.

As, used herein, the term "biological sample," or "sample," refers to a complex mixture obtained from a source, often a patient, and more specifically a human patient. In most instances, samples, or biological samples that are to be processed and analyzed by the disclosed methods, will be biological fluid samples.

As used herein, the term "biological fluid sample" refers to a biological sample that is obtained from a subject as a fluid. Nonlimiting examples of suitable biological fluid samples include, in no particular order, blood, serum, plasma (including plasma made through the addition of either EDTA or heparin to whole blood), urine, saliva, cerebrospinal fluid, cytosol, interstitial fluid, and the like.

The term "small molecule," or "small molecule analyte," as used herein, refers to a low molecular weight chemical compound that may function, or serve to regulate, a biological process or processes, or may otherwise be known to be "biologically active." In general, most "small-molecules" are organic compounds, including naturally-occurring compounds and exogenously introduced drugs having a molecular weight of about 900 Daltons (mass units) or less. Many, but not all, small molecules are small enough to diffuse across cell membranes so that they can reach intracellular sites of action.

The term "macromolecule," as used herein, refers to a molecule that contains a very large number of atoms, such as a protein. In general, macromolecules have molecular weights that are measured in thousands of Daltons (mass units), or "kilodaltons."

As used herein, the term "free," when referring to an analyte in a biological fluid sample, generally means not bound by (i.e., "unbound" by) protein or some other larger biological binding moiety. In most instances herein, the term "free" represents one state in which a given analyte exists within a biological fluid sample, with the other state being referred to as "bound" or "protein-bound."

The term "binding protein" as used herein, refers to a protein moiety that binds a particular analyte, or set of analytes. In some instances the term "binding protein" refers to a protein that specifically (and often tightly) binds a particular analyte, or set of analytes, thereby reducing and limiting the amount of this analyte, or set of analytes, that is free within a biological fluid sample. In other instances, the term "binding protein" refers to proteins that non-specifically (and often weakly) bind a particular analyte. Given the action of binding proteins, the amount of a free analyte that is found in a biological fluid sample is determined by the total amount of the analyte present, the total amount of specific and non-specific binding proteins present, and the relative binding affinity of these specific and non-specific binding proteins for this analyte.

As used herein, the term "specific binding" refers to a relatively strong and specific interaction between a binding protein and a particular analyte. In instances of specific binding it is generally understood that the "specific binding protein" possesses one or more "binding pockets" that are complementary to a particular analyte.

The term "non-specific binding" refers to a relatively weak and often non-specific interaction between a binding protein and a particular analyte. In such instances, there is a generalized attraction between the binding protein and a specific analyte, and there may or may not be a "binding pocket" for the specific analyte on or in the non-specific binding protein.

As used herein, the term "cognate," when used to describe an analyte or binding protein, refers to the relatedness between an analyte and the binding protein that evolved to bind it. The term can be used to describe or limit what analyte(s) will bind to a specific binding protein, or conversely, what binding protein(s) will effectively bind a specific analyte. For example, when 25-hydroxy vitamin D3 and 25-hydroxy vitamin D2 are being considered as analytes, a cognate binding protein is vitamin D binding protein (VDBP), a member of the albumin gene family of proteins encoded by the GC gene. VDBP evolved to bind vitamin D3 (cholecalciferol) and vitamin D2 (ergocalciferol) and 25-hydroxylated forms, 25-hydroxy vitamin D3 and 25-hydroxy vitamin D2, and serves as a circulating reservoir for these molecules, as well as a means to transport these molecules throughout the body.

The term "aqueous," as used herein, means containing mostly water, typically as a solvent or medium. Consequently, as used herein, the term "aqueous solution" means a liquid medium comprised mostly of water and various dissolved or suspended components. The term "aqueous" is often used in contrast to the term "organic," as in "organic solvent."

The term "organic" as used herein to describe solvents, means relating to chemical compounds or compositions containing carbons, and especially hydrocarbons, and derivatives thereof. Examples of organic solvents can include water-miscible solvents, such as the alcohols like methanol or ethanol, which form a homogenous mixture when mixed with water. Alternatively, "immiscible" solvents as used herein, means solvents that are not miscible, or that incapable of being mixed with water or aqueous solutions. Examples of immiscible combinations include the proverbial "oil and water," and other combinations of organic fluids and aqueous solutions. In some examples, an organic solvent can comprise greater than 10% organics, greater than 20% organics, greater than 30% organics, greater than 40% organics, greater than 50% organics, greater than 60% organics, greater than 70% organics, greater than 80% organics, greater than 90% organics, or about 100% organics.

"Size-exclusion chromatography," or "SEC," as used herein, refers to a chromatographic method in which molecules in solution are separated by their size, which generally correlates with their molecular weight. Size-exclusion chromatography involves the passage of a liquid "mobile phase" through a porous, solid "stationary phase," and the stationary phase is usually comprised of particles, especially spherical or globular particles, that are physically contained within a column. When the mobile phase comprises an aqueous solution, the size-exclusion technique is commonly referred to as "gel-filtration chromatography." Whereas, when the mobile phase comprises an organic solvent, the size-exclusion technique is commonly referred to as "gel-permeation chromatography." The principal use of gel-filtration chromatography is the fractionation of proteins, protein complexes, and other water-soluble polymers, by size, while gel permeation chromatography is generally used to analyze the molecular weight distribution of organic-soluble polymers. (See *Modern Proteomics—Sample Preparation, Analysis and Practical Application* by Hamid Mirzaei and Martin Carrasoco (Eds.), ISBN 978-3-319-41448-5 Springer International Publishing (2016) Chapter 5, Improving Proteome Coverage by Reducing Sample Complexity via Chromatography by Uma Kota, et al., Section 5.4, Size Exclusion Chromatography, pp. 93-94.)

In both forms of size-exclusion chromatography (i.e., gel-filtration and gel-permeation chromatography), the stationary phase is sometimes referred to as a "size-exclusion chromatography matrix," and the material used to form the size-exclusion chromatography matrix is often referred to as the "size-exclusion chromatography media," or simply the "chromatography media" or "size-exclusion media," or the "size-exclusion chromatography resin," or simply the "chromatography resin" or "size-exclusion resin."

The terms "desalting" and "buffer exchange," as used herein, generally refer to methods used to separate macromolecules from substantially smaller molecules (e.g., salts and buffering compounds) by size-exclusion chromatography. The methods used in desalting and buffer exchange are nearly identical. The difference in the names reflects a difference in the end goal of the process; either to remove or reduce salts from the mobile phase, or to change out buffering agents in the mobile phase, respectively. Both methods are based on gel filtration chromatography, also sometimes called "molecular sieve chromatography," which is a form of size-exclusion chromatography.

Desalting and buffer exchange both entail recovering the components of a sample in whatever buffer is used to pre-equilibrate the small, porous polymer spherical beads or globules that make up the chromatography media (or resin) used in the desalting or buffer exchange process. Desalting occurs when salts and other small molecules are removed from a sample in exchange for water, when the resin being used is pre-equilibrated in water. Buffer exchange occurs when the buffering agents in a sample are exchanged for those of another buffer, which was used to pre-equilibrate the resin.

Size-exclusion chromatography media used for desalting or buffer exchange is commonly enclosed within columns, the ends of which are generally defined by porous disks that allow the free passage of solutions and solvents through the column and its enclosed size-exclusion chromatography media. These size-exclusion columns are found in a wide variety of sizes; the size and "bed volume" of which is generally chosen to match the volume of the sample to be applied to the column, or to the total amount of solutes within the sample applied to the column.

As used herein the term "wash" or "wash step" refers to the passage of a solution (i.e., wash solution) through a size-exclusion column after a sample has been applied to the column. The purpose of a "wash" or "wash step" is generally to remove unwanted materials and components from the column prior to "elution" or the "elution step." In some cases the wash step is performed with water, in other cases it is performed with a buffered aqueous solution.

The term "elution" or "elution step" as used herein, refers to the step in which wanted or desired materials and components are released and removed from a size-exclusion column. During standard desalting or buffer exchange "molecular sieve chromatography," the desired materials and components (usually macromolecules) generally pass through and elute from the size-exclusion column without a significant wash or specialized elution step, while the undesired materials (usually salts or buffering agents) are retained within the bed of the size-exclusion column. As will be seen below, the presently disclosed methods differ from standard methods of "molecular sieve chromatography," in that the undesired materials (i.e., protein-bound analytes) pass through and elute from the size-exclusion column without a significant wash or specific elution step, while the desired materials (i.e., free target analytes) are retained within the bed of the size-exclusion column, and must be eluted with a specific elution step performed with an organic solvent.

According to various embodiments of the present disclosure, the methods described provide novel techniques to separate a free (i.e., non-protein-bound) fraction of a target analyte (free target analyte) from a protein-bound fraction of the same target analyte (protein-bound target analyte) prior to quantification. The methods described herein can conceivably be used for any target analyte, target analytes, or group of target analytes, that partition between a protein-bound fraction and a free (i.e., non-protein-bound) fraction in a biological sample, such as a biological fluid. However, these methods can be particularly useful when a free target analyte has a tendency to nonspecifically attach (i.e., adsorb, adhere, or otherwise bind to, or become immobilized on) to a surfaces while in the free form. In many cases, such surface can include those commonly contacted by biological fluid samples during sample handling, sample preparation, or sample analysis.

In some examples, the present techniques can be used to separate free from protein-bound steroids, secosteroids, phytosterols, drugs, or metabolites thereof. In other examples, the present techniques can be used to separate free from protein-bound lipid-soluble hormones, including androgens and estrogens, lipid soluble vitamins, such as the various forms of vitamin D, and metabolites thereof. In yet other examples, the present techniques can be used to separate free from protein-bound small molecule analytes, including lipophilic drugs such as phenytoin, digoxin, carbamazepine, valproic acid, disopyramide, paclitaxel, mycophenolic acid, mycophenolate mofetil, lidocaine, xylocaine, lignocaine, and metabolites thereof. These methods can also be used, for example, to separate free from protein-bound oligopeptides or peptides. Nonlimiting examples can include free Insulin-like growth factor I (IGF 1), free Insulin-like growth factor 2 (IGF 2), free insulin, free thyroglobulin, free cardiac troponin (cTn), and the like. Additionally, in some examples the methods can be utilized to separate free target analyte from antibody-bound target analyte. One example of such a target analyte assay is prolactin, where in some patients an antibody-bound macroprolactin molecule can be separated from an unbound antibody-free prolactin.

In further examples, the present techniques can be used to separate free forms of vitamin D, including free 25-hydroxy vitamin D3 and 25-hydroxy vitamin D2, for example, from protein-bound forms of these same analytes, including those forms bound by vitamin D binding protein (VDBP) and/or bound by serum albumin. Furthermore, the present techniques can thereby allow for the direct, qualitative and/or quantitative detection and determination of these free forms of vitamin D by any suitable analytical technique, such as, for example mass spectrometry, either with or without derivatization of the target analyte.

In other examples, the present techniques can be used for separating free forms of testosterone, dihydrotestosterone (DHT), estradiol and cortisol from protein-bound forms, thereby allowing for the direct, qualitative and/or quantitative detection and determination of these free forms of testosterone, DHT, estradiol and cortisol by any suitable analytical technique, such as, for example mass spectrometry, either with or without derivatization of the target analyte.

There are often clinically-important reasons to determine how much of a particular analyte exists in a free state or form, and there are many technological challenges associated with diagnostic assays designed to make such determinations. Additionally, certain classes of small molecule analytes present particular challenges to the laboratorian attempting to quantify them. For example, lipophilic analytes can nonspecifically attach to surfaces while in the free form, but not while in the protein-bound state. When such free analytes attach to surfaces commonly contacted by biological fluid samples during sample handling, sample preparation, and sample analysis (e.g., test tubes, centrifuge tubes, 96-well plates, filtering devices and membranes, instrument tubing, detection cells, etc.), the amount or concentration of such free analytes present in a sample will be underestimated or the analyte will be completely lost and will be undetectable.

When measuring the amount of free analyte in biological fluid sample, one aim of the laboratorian is to use techniques that do not disturb the corresponding protein-bound fraction of the analyte. In contrast, methods of measuring "total" amounts of a particular analyte are designed to specifically disrupt the protein-bound fraction to release the analyte so that total concentration (free plus protein-bound fractions) can be quantified.

The "free hormone hypothesis" holds that only hormones which are not bound to high-affinity carrier proteins are able to enter cells and exert biological activity [Mendel, C. M. *Endocr. Rev.* 1989, 10(3), 232-274]. This hypothesis has been well established for certain hormones, such as sex steroid and thyroid hormones [Ibid.; Mendel, C. M. *J. Androl.* 1992 13(2), 101-116; Vermeulen, A., et al., *J. Clin. Endocrinol. Metab.* 1999, 84(10), 3666-3672]. Consequently, the separation of free hormone from protein-bound hormone can facilitate quantitation of free hormone levels, and allow for determination of hormonal deficiencies (hypoandrogenism, hypothyroidism, infertility, etc.) or excess (hyperthyroidism, hyperandrogenism, polycystic ovary disease, etc.).

As noted above, the size-exclusion chromatography media (i.e., resin) incorporated into size-exclusion columns can be configured in a variety of forms, such as small beads, globules, or other geometrical structures (i.e., media). Such media can be packed together in a column to form a size-exclusion chromatography matrix or "bed." As such, the media is packed in the matrix or bed in such a way as to maintain small spaces around the outsides of the media, which are referred to as "interstitial spaces." The individual beads or globules of the media are themselves porous, and the size of the pores within the media determines the size of molecules that can penetrate into these pores and permeate and percolate through the interior of the media that make up the matrix.

Similarly, it is ultimately the size of the pores within the media that determines how large a molecule or molecular complex is excluded from the interior pores, which are thereby limited to the interstitial spaces around and between the media that make up the matrix. This property to exclude molecules or molecular complexes above a certain size is characterized by the so-called "molecular weight cut-off" (or "MWCO") of the particular size-exclusion chromatography media. Molecules and molecular complexes with a molecular weight greater than the MWCO of the media are unable to readily enter the pores and therefore remain in the interstitial spaces, while molecules with a molecular weight smaller than the MWCO penetrate the pores and permeate and percolate through the interior of the media. MWCO values of size-exclusion chromatography media are generally specified in units of mass, such as kilodaltons, or kDa.

While not wishing to be bound by theory, it is generally believed that in standard size fractionation or desalting methods, small molecules below a certain molecular size or radius—that is with masses smaller than the MWCO—penetrate into, and permeate and percolate through, the pores in the interior of the media, while larger molecules—that is molecules and complexes with masses greater than the MWCO—are excluded from the pores and remain in the interstitial spaces. The molecules and molecular complexes that are excluded from the pores in the media remain in the interstitial spaces, and, when a solution is passed through the column, can thus freely pass around the media to pass through the column bed. In contrast, passage of the smaller molecules through the column bed is delayed because these smaller molecules enter the pores of the media and therefore pass through an effectively larger "bed volume" before eluting from the column.

In some examples, the presently disclosed methods can utilize various types of desalting columns, and such methods can be distinguished from standard desalting procedures that utilize such columns. During standard desalting procedures the "desired" macromolecular components of a mixture flow through the interstitial spaces of the size-exclusion chromatography media within the desalting column, and are obtained in the initial eluent (i.e., "flow through") from the column. The "undesired" small molecule components (e.g., salts and buffering agents), however, are retained within the pores of the size-exclusion chromatography media within the desalting column and are discarded along with the column. In contrast, in the presently disclosed methods, the "desired" free target analytes are retained via attachment within the pores of the size-exclusion chromatography media within the desalting column, while the "undesired" macromolecular complexes (i.e., binding proteins with bound target analytes) are found in the initial eluent (i.e., "flow through") from the column, which is then discarded as biological waste. As such, the presently disclosed methods differ from such known size fractionation or desalting methods in the way the free and protein-bound forms of a target analyte are both separated and retrieved after being applied to a size-fractionation column. More specifically, while not wishing to be bound by theory, in the presently-disclosed methods a biological fluid sample is applied to the size-fractionation column and the desired free target analytes of interest penetrate into the pores of the size-fractionation media and attach thereto, while the undesired protein-bound forms of the same target analyte remain in the interstitial spaces, and thus are readily washed through the column and discarded. The free target analyte molecules attached to the chromatography media can be subsequently removed from the size-exclusion chromatography media by eluting with an organic solvent that is passed through the column and the chromatography media.

In another example, the presently disclosed methodology differs from traditional desalting procedures using desalting columns and devices in the intentional use of organic solvents to elute the "desired" free target analytes retained by attachment within the pores of the size-exclusion chromatography media within the desalting column or device after the "undesired" macromolecular components and protein-bound target analytes have eluted from the desalting column in the aqueous flow through. The intentional switch from an aqueous solvent system during the loading, binding and washing steps to a fully-organic solvent system during the elution step, in which the adsorbed or immobilized "desired" free (i.e., non-protein-bound) target analytes are retrieved from the size-exclusion matrix, has no equivalent in traditional desalting or buffer-exchange procedures. This feature of the disclosed methods represents a new use of desalting columns or devices that is contrary to the teachings in the art, that suggests that the size-exclusion resin should not be subjected to fully organic solvent systems. See, for example, "Answer ID: E12864" in the Zeba™ Product FAQs, available from ThermoFisher Scientific on the world wide web at: https://www.thermofisher.com/search/results?query=E12864&focusarea=Searh%20All (as accessed on Nov. 4, 2018). Wherein, in response to the Question: "Are Zeba™ columns compatible with salts/organics?" The answer provided (i.e., E12864) was: "Yes, Zeba™ columns are compatible with most salts. The resin is stable to some organics. *As organics may affect performance, we suggest using less than* 10% *organics.*" (Emphasis added.)

Additionally, while not wishing to be bound by theory, it is believed that the methods disclosed herein solve certain problems that result from the non-specific adsorption or immobilization of free target analytes to/on surfaces and substrates commonly encountered by biological samples during sample handling, sample preparation and sample analysis. Specifically, it has been observed that certain hydrophobic free analytes have a propensity to adsorb or become immobilized on surfaces and substrates commonly contacted by biological fluid samples during sample handling, sample preparation and sample analysis, such as, for example test tubes, centrifuge tubes, 96-well plates, filtering devices and membranes, and instrument tubing and detection cells. This phenomenon can lead to the amount or concentration of such free analytes being underestimated or even completely lost and therefore undetectable. This problem is exacerbated when the concentrations of the free analytes are already low in the biological fluid sample before processing. The presently disclosed methods solve this problem by employing organic solvents during an elution step, and these organic solvents act to dissociate any such bound, adsorbed or immobilized target analytes from the surfaces to which they are bound, adsorbed or immobilized.

For example, it is known that certain small-molecule analytes, and especially lipophilic small-molecule analytes, such as "free" 25-hydroxy vitamin D2 or 25-hydroxy vitamin D3 and their metabolites, readily adsorb to the surfaces and substrates commonly encountered by biological samples during sample handling, sample preparation and sample analysis. In some instances it is possible to document the gradual reduction in free target analyte in solution by simply allowing a biological sample to remain in contact with particular surfaces and substrates commonly used during sample handling, sample preparation and sample analysis, and to quantify the amount of free target analyte in solution at given intervals of time. The binding or adsorption of such lipophilic target analytes presents a problem for the accurate quantification of such target analytes and naturally leads to the underestimation of the amount of the free target analyte initially present in the biological fluid sample.

The methods disclosed herein solve the problem of non-specific adsorption and binding of free analytes to the surfaces and substrates in at least two ways: (1) By rapidly and directly applying the biological fluid sample to the size-exclusion chromatography media or matrix, thereby reducing sample handling and exposure of the biological fluid sample to surfaces and substrates that would adsorb or bind free target analyte; and (2) by intentionally eluting the target analytes from the size-exclusion chromatography media or matrix with an organic solvent in which the target analyte is soluble and can remain solubilized.

Finally, while not wishing to be bound by theory, it is believed that the presently disclosed methods effectively maintain the stability of macromolecular complexes formed between a particular target analyte and its cognate binding protein(s), such that the amount of that same analyte that exists in a non-protein-bound (i.e., free) state in a biological fluid sample is accurately determined. In particular, it is believed that the presently disclosed methods maintain the equilibrium between the free and bound fractions of the target analyte until the biological fluid sample is applied to the size-exclusion column or device, by purposefully eliminating sample handling steps that might lead to destabilization of bound analyte complexes. Specifically, the biological sample to be analyzed is not diluted prior to being directly applied to the size-exclusion chromatography media or matrix used to separate the free fraction of target analyte from the corresponding protein-bound fraction of target analyte. The biological sample is also not filtered, precipitated, or otherwise fractionated, prior to be being directly applied to the size-exclusion chromatography media or matrix. The importance of maintaining the stability of such macromolecular complexes formed between a particular analyte and its cognate binding protein(s) and the equilibrium between free and bound analyte fractions cannot be overstated, since any disruptions (prior to or while the sample containing the protein-bound analyte resides within the size exclusion media) would release protein-bound analyte(s) from the their cognate binding proteins, leading to an overestimation of the amount of free analyte present in the biological fluid sample, and therefore an inaccurate test result.

Example Embodiments

Before embodiments of the present methods, kits and compositions are disclosed and described, it is to be understood that these disclosed embodiments are not limited to the particular process steps and materials disclosed herein, but should be extended to equivalents thereof, as would be recognized by those ordinarily skilled in the relevant arts. It should also be understood that terminology employed herein is used for the purpose of describing particular embodiments only and is not intended to be limiting.

Reference will now be made in detail to particular embodiments of the disclosed methods, kits and compositions.

It has been discovered that free (i.e., non-protein-bound) forms of certain target analytes that distribute between a protein-bound fraction and a free, or non-protein bound fraction, can be separated and isolated from biological fluid samples using a method that involves a novel use of a size exclusion chromatography matrix. In general, a sample comprising a complex mixture that includes a target analyte present in both a free form and a protein-bound form is directly applied to, and passed through a size-exclusion chromatography matrix with a molecular weight cut off sufficient to allow the free form of the target analyte to permeate into the size-exclusion chromatography matrix, whereupon the free target analyte adsorbs to, or otherwise becomes immobilized within or on, the size-exclusion chromatography media that makes up the size-exclusion chromatography matrix. The corresponding protein-bound target analyte in macromolecular complexes pass through the size-exclusion chromatography matrix column, and any protein-bound target analyte remaining can be removed from the column, such as by "washing it away" with an aqueous wash step. The media-adsorbed or immobilized free target analyte is subsequently eluted from the size-exclusion chromatography matrix using, for example, a suitable organic solvent. One nonlimiting example category of suitable target analytes can include, without limitation, lipophilic small-molecule target analytes.

While not wishing to be bound by any one theory, it is believed that upon permeation into the pores of the size-exclusion chromatography matrix, the free target analyte attaches to the internal spaces within the media of the matrix, while protein-bound target analyte is excluded from the internal spaces of the media and remain in the interstitial spaces of the matrix, where they are readily passed through the size-exclusion chromatography matrix as an intact macromolecular complex formed between the analyte and its cognate binding protein. Thus, the environment within the column can include any conditions that allow the protein-bound target analyte to be maintained as an intact macromolecular complex, and any such environment/conditions is considered to be within the present scope.

As these macromolecular complexes are precluded from entering the pores of the size-exclusion chromatography media due to size restrictions, conditions that might result in the destabilization and disassociation of macromolecular complexes would be expected to facilitate the release of the associated protein-bound target analyte. Such released target analyte is of a size that can then enter the pores of the size-exclusion chromatography media, which would then be indistinguishable from the free target analyte, resulting in an inaccurate measurement of the free target analyte. Consequently, the presently disclosed methods are designed to maintain an environment within the column and its interstitial spaces that retains the stability of the macromolecular complexes formed between the target analyte and its cognate binding protein(s) which such macromolecular complexes are present during the loading and aqueous wash steps.

After loading, the size-exclusion chromatography matrix can be washed according to any protocol that removes substantially all non-target proteins and protein-bound target analytes (i.e. protein macromolecular complexes), while not disturbing the adsorbed free target analyte that remains immobilized within pores, or on surfaces of, the size-exclusion chromatography media. One nonlimiting example can include washing with a sufficient quantity of any suitable aqueous wash solution, usually a buffered wash solution.

The bound or immobilized free target analyte is then eluted from the size exclusion chromatography matrix with a sufficient volume of an appropriate organic solvent solution, wherein the organic solvent solution quantitatively elutes the bound, adsorbed or otherwise immobilized free target analyte. In certain embodiments, the organic solvent solution is a pure immiscible organic solvent or mixture of immiscible organic solvents containing little to no water. In other embodiments the organic solvent solution may contain a miscible organic solvent or combination of miscible organic solvents, and some amount of water, such as, for example less than about 50%, 40%, 30%, 20%, 10%, 5%, or 1% water. In all encompassed embodiments, the organic solvent solution quantitatively elutes the bound, adsorbed or otherwise immobilized free target analyte.

The eluted target analyte is then detected with any suitable analytical technique, such as, for example, antibody-based techniques (e.g. radioimmunoassay, fluorogenic immunoassay, magnetic immunoassay, enzyme-linked immunoassay, or surface plasmon resonance), mass spectrometry, or the like, in some cases following chemical derivatization of the target analyte to increase the sensitivity of detection.

Although the disclosed methods are related to both size-exclusion chromatography and reversed-phase or hydrophobic interaction chromatography, the disclosed methods uniquely combine both chromatographic techniques in a novel manner to solve a long-recognized technical problem of separating free (i.e., unbound or non-protein bound) target analytes from protein-bound target analytes, when those analytes (a) partition between free and protein-bound states in biological samples and (b) have a propensity to bind, adsorb, adhere to, or otherwise become immobilized on surfaces and substrates, particularly surfaces and substrates encountered by biological samples during sample handling, sample preparation and sample analysis procedures. Moreover, the disclosed methods represent a new use for size-exclusion chromatography media that, in some cases, is specifically discouraged, or taught away from, in accompanying product literature. Thus, the disclosed methods, which utilize an organic solvent elution step with resins routinely used for desalting aqueous samples with aqueous solvents, represents an unorthodox or unconventional, and therefor novel, use of such desalting resins.

Although the disclosed methods have been found to work, and are thus illustrated, in separating free forms of 25-hydroxy vitamin D3, 25-hydroxy vitamin D2 and testosterone from their protein-bound counterparts, these methods can be applied to a wide range of other target analytes that are present in both free and protein-bound forms in biological samples. As noted, these methods are especially useful for those target analytes that have a propensity to bind, adsorb, adhere to, or otherwise become immobilized on surfaces and substrates, particularly surfaces and substrates encountered by biological samples during sample handling, sample preparation and sample analysis procedures.

The disclosed methods are also sufficiently gentle so as not to disrupt the complexes formed by the binding of certain target analytes by cognate and other physiologically relevant binding proteins (e.g. weakly bound to albumin, which is a carrier protein for many of the analytes for which measurement of free fraction is warranted). This is particularly important when such complexes are unstable, or subject to disruption through established methods of sample preparation and handling (e.g. albumin), and through existing chromatographic separation methods.

An important aspect of the disclosed method that helps maintain the stability of complexes formed by the binding of certain target analytes by cognate and other physiologically relevant binding proteins is that undiluted sample is applied directly to the size-exclusion chromatography media, which is prepared and equilibrated in an aqueous solution. This aspect can also be beneficial when the complexes formed by the binding of certain target analytes by cognate and other physiologically relevant binding proteins are not stable to changes in buffer, pH, or salt concentrations that occur during commonly employed sample preparation procedures, such as dilution, ultrafiltration, especially using techniques allowing extended time for the samples to be in an open container (e.g., ultrafiltration, dialysis), which can lead to the changes in the sample pH and increase levels of oxidation.

Indeed, the direct application of undiluted samples to the size-exclusion chromatography media, as taught herein, sets the presently disclosed methods apart from other methods in the prior art designed to separate and quantify free from protein-bound analytes, such as, for example, the methods disclosed in U.S. Pat. No. 4,456,689 ("Competitive protein binding assay using an organosilane-silica gel separation medium," issued Jun. 26, 1984 to Witty and Astill). In every example disclosed in U.S. Pat. No. 4,456,689, the starting serum sample is diluted prior to it being passed through a bed of chromatography media comprising octadecylsilane covalently bonded to silica gel particles. The amount of sample dilution ranges from 3.275-fold in Example 6 to 30.3-fold in Example 3. While not wishing to be bound by theory, it is believed that this dilution of samples taught in U.S. Pat. No. 4,456,689, as well as the accompanying changes in buffer, pH, or salt concentrations occurring as a result of the sample preparation and dilution steps, effectively disturbs the equilibrium of binding of a portion of the complexes formed by the binding of certain target analytes by cognate and other physiologically relevant binding proteins. These disturbances can result in the release of bound analytes and a resulting overestimation of the amount of free analyte in the sample.

The methods disclosed herein have broad potential application, and can be used to separate a large variety of free from protein-bound lipophilic steroids, secosteroids, phytosteroids, and metabolites thereof, as well as free from protein-bound drugs, and their metabolites. Consequently, the methods disclosed herein have the potential for use in separating free from protein bound analytes from such diverse classes as hormones, including androgens, estrogens, thyroid hormones (free T3 and/or free T4), corticosteroids, and their metabolites, as well as certain drugs, including, for example phenytoin, digoxin, carbamazepine, valproic acid, disopyramide, paclitaxel, mycophenolic acid, mycophenolate mofetil, lidocaine, xylocaine, lignocaine, and their metabolites, in their free form from their protein-bound form(s).

The separation methods disclosed herein can be used to facilitate analytical procedures specifically designed to quantify free forms of analytes, including steroids, secosteroids, phytosteroids, drugs, or metabolites thereof, including such classes of analytes as hormones, including androgens, estrogens, thyroid hormones (free T3 and/or free T4), corticosteroids, and their metabolites, as well as free forms of certain drugs, including, for example phenytoin, digoxin, carbamazepine, valproic acid, disopyramide, paclitaxel, mycophenolic acid, mycophenolate mofetil, lidocaine, xylocaine, lignocaine, and metabolites thereof.

Moreover, the separation methods disclosed herein can be used to facilitate analytical procedures specifically designed to quantify free forms of target analytes when those target analytes are small molecules that bind, adsorb, or otherwise become immobilized on size exclusion chromatography media, and those target analytes exist in biological fluid samples in both a free state, and a protein-bound state in which they are bound by cognate binding proteins or other non-specific binding proteins. For example, the separation methods disclosed herein can be used to facilitate analytical procedures specifically designed to quantify free forms of target analytes that are bound by specific binding proteins such as vitamin D-binding protein (VDBP), sex hormone-binding globulin (SHBG), corticosteroid-binding globulin (CBG; which is also known as transcortin or serpin A6), insulin-like growth factor binding proteins 1-6 (IGFBP1-IGFBP6), alpha-2-macroglobulin, and/or are non-specifically bound by serum albumin, or other abundant serum proteins. Specifically, the separation methods disclosed herein can be used to facilitate analytical procedures specifically designed to quantify free forms of steroid hormones that are bound by CBG/transcortin, such as glucocorticoids and progestins, free forms of steroid hormones that are bound by SHBG, such as the various forms of androgens and estrogens, or insulin-like growth factors that bind to IGFBP1, IGFBP2, IGFBP3, IGFBP4, IGFBP5 or IGFBP6.

Additionally, the separation methods disclosed herein can be used to facilitate analytical procedures specifically designed to quantify free forms of target analytes that are bound by specific antibodies or autoantibodies.

The present disclosure provides methods of separating free target analyte from protein-bound target analyte in an aqueous sample. Such methods can include obtaining an aqueous sample that contains a target analyte in a free form (free target analyte) and the target analyte in a protein-bound form (protein-bound target analyte) in which the target analyte is bound to a target analyte binding protein, passing the aqueous sample through a size exclusion chromatography matrix with a molecular weight cut off sufficient to allow the free target analyte to permeate into pores of the size exclusion chromatography matrix and exclude the protein-bound target analyte, whereupon the free target analyte adheres to and is immobilized by the size exclusion chromatography matrix and the protein-bound target analyte does not adhere to by the size exclusion chromatography matrix, separating the free target analyte from the protein-bound analyte by removing the protein-bound target analyte from the size exclusion chromatography matrix, and eluting the free target analyte from the size exclusion chromatography matrix with an organic solvent.

Such methods can be used the protein-bound target analyte is bound by more than one target analyte binding protein.

Such methods can further comprise washing the size exclusion chromatography matrix with an aqueous wash solution before eluting the free target analyte from the size exclusion chromatography matrix with an organic solvent.

Such methods are particularly useful when the target analyte is a molecule that nonspecifically adsorbs or adheres to surfaces when in the free form. For example, such methods are particularly useful when the target analyte to be separated is a lipophilic small molecule that nonspecifically adsorbs or adheres to surfaces while free, or after having been separated from its cognate or other relevant binding proteins.

Such methods can be used to separate free from protein-bound forms of steroids, secosteroids, phytosteroids, or metabolites thereof. They can be used to separate free from protein-bound forms of estrogens and androgens, or metabolites thereof, including testosterone and dihydrotestosterone, estradiol and cortisol. They can be used to separate free from protein-bound forms of vitamins and metabolites of vitamins. They can, and have, been used to separate free from protein-bound forms of 25-hydroxy vitamin D3 or 25-hydroxy vitamin D2. They can also be used when the target analyte is a lipophilic prodrug, drug, or some metabolite thereof. For example, they can be used when the target analyte is phenytoin, digoxin, carbamazepine, valproic acid, disopyramide, paclitaxel, mycophenolic acid, mycophenolate mofetil, lidocaine, xylocaine, lignocaine, or a metabolite thereof. They can also be used when the target analyte is an oligopepetide or peptide, when that oligopepetide or peptide is found both in a free form and bound by a binding protein.

Such methods can sometimes be used to simultaneously separate the free from protein bound forms of multiple lipophilic analytes. For example, the methods can be used to simultaneously separate free from protein bound forms of various steroids, secosteroids, phytosteroids, drugs, or a metabolite thereof. For example, these methods can be used to simultaneously separate free from protein-bound forms of vitamin D3 (cholecalciferol) and vitamin D2 (ergocalciferol), including their 25-hydroxylated forms, 25-hydroxy vitamin D3 and 25-hydroxy vitamin D2, and their 1,25-hydroxylated forms, 1,25-dihydroxy vitamin D3 and 1,25-dihydroxy vitamin D.

In these methods, the free target analyte, or additional free target analytes are soluble in the organic solvent that is used in the elution step. For example, the organic solvent used to elute the free target analyte or additional free target analytes can be an ether, such as methyl tert-butyl ether or diisopropyl ether. In some embodiments, the organic solvent used to elute the free target analyte or additional free target analytes can be an alcohol, such as methanol. Further examples can include ethyl acetate, hexane, dimethyl ether, diethyl ether, dipropyl ether, ethyl methyl ether, sec-butyl-methyl ether, heptane, ethanol, butanol, isopropyl alcohol, and the like.

In these methods, the size exclusion chromatography matrix employed can comprise size exclusion chromatography resin composed of a polymer of macroporous cellulose, cross-linked dextran, cross-linked agarose, agarobiose, porous styrene divinylbenzene, cross-linked hydroxypropylated dextran, copolymers of acrylamide and N,N'-methylene-bis-acrylamide, copolymers of dextran and cross-linked agarose, or cross-linked allyl dextran and N,N'-methylene-bis-acrylamide, including combinations or derivatives thereof. In specific embodiments the polymer of size exclusion chromatography matrix employed is macroporous cellulose.

In these methods, the polymer of the size exclusion chromatography resin can have a molecular weight cut off of about 1 kDa, about 2 kDa, about 5 kDa, about 7 kDa, about 10 kDa, about 15 kDa, about 20 kDa, about 30 kDa, about 40 kDa, or about 50 kDa. In specific embodiments the size exclusion chromatography matrix polymer has a molecular weight cut off of about 5 kDa, about 7 kDa, or about 10 kDA.

In these methods, the aqueous sample can be a biological fluid such as serum, plasma, urine, cerebrospinal fluid, and saliva, and, if plasma, the plasma can be prepared through the addition of EDTA or Heparin to whole blood.

In these methods the target analyte can be soluble in the organic solvent used to elute the free target analyte from the size exclusion chromatography matrix, and the organic solvent used to elute the free target analyte from the size exclusion chromatography matrix is methyl tert-butyl ether, diisopropyl ether, methanol, or combinations thereof.

In certain embodiments of these methods where the free target analytes to be separated are 25-hydroxy vitamin D3 and free 25-hydroxy vitamin D2, the polymer of the size exclusion chromatography matrix can be macroporous cellulose, and the organic solvent used to elute free 25-hydroxy vitamin D3 and free 25-hydroxy vitamin D2 from the macroporous cellulose size exclusion chromatography matrix is methyl tert-butyl ether, diisopropyl ether, methanol, or combinations thereof.

In certain embodiments of these methods where the free target analyte to be separated is free testosterone, the polymer of the size exclusion chromatography matrix can be macroporous cellulose, and the organic solvent used to elute free testosterone from the macroporous cellulose size exclusion chromatography matrix is methyl tert-butyl ether, diisopropyl ether, methanol, or combinations thereof.

In some embodiments of these methods, the methods further comprise drying the eluted free target analyte contained in the organic solvent prior to further processing and analysis. In some sub-embodiments, the dried target analyte is redissolved and derivatized prior to analysis. In other sub-embodiments, the dried target analytes is redissolved analyzed directly, without derivatization.

In some embodiments of these methods, resdissolved and underivatized free target analyte that has been separated by the disclosed methods is analyzed by an immunoassay procedure, such as, for example, radioimmunoassay, fluorogenic immunoassay, magnetic immunoassay, enzyme-linked immunoassay, or surface plasmon resonance.

In some embodiments of these methods, the eluted free target analyte, derivatized or not, is analyzed by mass spectrometry. In some sub-embodiments, the eluted free target analyte, derivatized or not, is subjected to separation by high pressure liquid chromatography (HPLC), or another suitable chromatographic method, prior to analysis by mass spectrometry.

In some embodiments of these methods, an isotopically labeled target analyte is added to the organic solvent used to elute the free target analyte prior to the elution step, or it is added to the eluent after the free target analyte is eluted from the size exclusion chromatography matrix. In some sub-embodiments this isotopically labeled target analyte is dried, redissolved and/or derivatized along with the eluted free target analyte. In those embodiments where such an isotopically labeled target analyte is added, it can be used as an internal control or standard that can be used to help quantify the amount of non-isotopically labeled free target analyte present in the biological fluid sample.

In some embodiments, the isotopically labeled target analyte and non-isotopically labeled free target analyte present in the biological fluid sample are simultaneously analyzed by mass spectrometry. In some sub-embodiments, the isotopically labeled target analyte and non-isotopically labeled free target analyte present in the biological fluid sample are subjected to separation by high pressure liquid chromatography (HPLC), or another suitable chromatographic method, prior to analysis by mass spectrometry. In some sub-embodiments, the mass spectrometry used for analysis is tandem mass spectrometry or triple quadrapole mass spectrometry. In certain sub-embodiments the mass spectrometry conducted is conducted in selected reaction monitoring mode or in multiple reaction monitoring mode.

In certain embodiments of these methods the size exclusion chromatography matrix is structurally configured to be contained in a device designed to be eluted by gravity, by centrifugation, or by a positive or negative pressure source. In certain embodiments the device may be configured for processing multiple samples at once. For example, the device for conducting the methods may be incorporated into a standard format, such as the ubiquitous 96-well format. In certain embodiments, the size exclusion chromatography matrix device used for separating free from protein-bound target analytes is 96-well spin desalting plate containing a size-exclusion resin, such as a macroporous cellulose resin. In specific embodiments, the size exclusion chromatography matrix device used for separating free from protein-bound target analytes is the 96-well Zeba™ Spin Desalting Plate with a 7 kDa molecular weight cut off from Thermo Scientific (ThermoFisher Scientific, Catalog No. 89807 or 89808). In other specific embodiments, the size exclusion chromatography matrix device used for separating free from protein-bound target analytes is the 96-well Zeba™ Spin Desalting Plate with a 40 kDa molecular weight cut off from Thermo Scientific (ThermoFisher Scientific, Catalog No. 87774 or 87775).

As will be appreciated by the skilled artisan, there are many advantages to such configurations—advantages that greatly facilitate the simultaneous processing of multiple experimental (e.g., patient) samples, along with the requisite control samples. The examples provided below give just one example of a preferred configuration for simultaneously processing multiple experimental (e.g., patient) samples, along with the requisite control samples, but there are many other configurations that can be employed, some of which will have their own distinct advantages.

The present disclosure also provides methods of separating free steroid, secosteroid, phytosteroid, oligopeptide, peptide, prodrug, drug, or metabolite thereof from protein-bound steroid, secosteroid, oligopeptide, peptide, prodrug, drug, or metabolite thereof, in a serum or plasma sample, including passing the serum or plasma sample through a size exclusion chromatography matrix with a molecular weight cut off sufficient to exclude albumin, immunoglobulins and proteins that bind said steroid, secosteroid, phytosteroid, oligopeptide, peptide, prodrug, drug, or metabolite thereof (i.e., a steroid, secosteroid, phytosteroid, oligopeptide, peptide, prodrug, drug, or metabolite thereof binding protein), washing the size exclusion chromatography matrix with an aqueous solution, and eluting free steroid, secosteroid, phytosteroid, oligopeptide, peptide, prodrug, drug, or metabolite thereof from the size exclusion chromatography matrix with an organic solvent.

In these methods, the size exclusion chromatography matrix employed can comprise size exclusion chromatography resin composed of a polymer of macroporous cellulose, cross-linked dextran, cross-linked agarose, agarobiose, porous styrene divinylbenzene, cross-linked hydroxypropylated dextran, copolymers of acrylamide and N,N'-methylene-bis-acrylamide, copolymers of dextran and cross-linked agarose, cross-linked allyl dextran and N,N'-methylene-bisacrylamide, or combinations or derivatives of such polymers. In specific embodiments the polymer of the size exclusion chromatography matrix employed is macroporous cellulose.

In these methods, the polymer of the size exclusion chromatography resin can have a molecular weight cut off of about 1 kDa, about 2 kDa, about 5 kDa, about 7 kDa, about 10 kDA, about 15 kDa, about 20 kDa, about 30 kDa, about 40 kDa, or about 50 kDa. In specific embodiments the size exclusion chromatography matrix polymer has a molecular weight cut off of about 5 kDa, about 7 kDa, or about 10 kDA.

In these methods, multiple steroids, secosteroids, phytosteroids, oligopeptide, peptide, prodrug, drug, or metabolites thereof, can be simultaneously separated, and the targeted steroid(s), secosteroid(s), phytosteroid(s), oligopeptide(s), peptide(s), prodrug(s) drug(s), or metabolite(s) thereof, is/are soluble in the organic solvent used to elute the free steroid, secosteroid, phytosteroid, oligopeptide, peptide, prodrug, drug, or a metabolite thereof, from the size exclusion chromatography matrix.

In these methods the organic solvent used to elute free steroid, secosteroid, phytosteroid, oligopeptide, peptide, prodrug, drug, or metabolite thereof, from the size exclusion matrix is selected from methyl tert-butyl ether, diisopropyl ether, methanol, or combinations thereof.

In these methods the aqueous sample can be a biological fluid such as serum, plasma, urine, cerebrospinal fluid, and saliva, and, if plasma, the plasma can be prepared through the addition of EDTA or Heparin to whole blood. In these methods the sample, especially when it is a serum or plasma sample, can be applied directly to the size exclusion chromatography matrix undiluted.

Following application of the sample to the size exclusion chromatography matrix in these methods, the size exclusion chromatography matrix is washed with an aqueous solution, such as distilled or deionized water, or a buffered aqueous solution. And, in some embodiments, one volume of size exclusion chromatography matrix is washed with about 1, 2, 3, 4, 5, 6, 7, 8, 9 or 10 volumes of aqueous solution after the sample is applied to it.

In these methods, after the size exclusion chromatography matrix is washed with an aqueous solution, the free steroid, secosteroid, phytosteroid, oligopeptide, peptide, prodrug, drug, or metabolite thereof, which is now adhered or immobilized on the size exclusion chromatography matrix, is eluted from one volume of size exclusion chromatography matrix with about 1, 2, 3, 4, 5, 6, 7, 8, 9 or 10 volumes of organic solvent.

In some embodiments of these methods, the eluted free steroid, secosteroid, phytosteroid, oligopeptide, peptide, prodrug, drug, or metabolite thereof in organic solvent is dried prior further processing and analysis. In some sub-embodiments, the dried free steroid, secosteroid, phytosteroid, oligopeptide, peptide, prodrug, drug, or metabolite thereof is redissolved and derivatized prior to analysis. In other sub-embodiments, the dried free steroid, secosteroid, phytosteroid, oligopeptide, peptide, prodrug, drug, or metabolite thereof is redissolved analyzed directly, without derivatization.

In some embodiments of these methods, resdissolved and underivatized free steroid, secosteroid, phytosteroid, oligopeptide, peptide, prodrug, drug, or metabolite thereof is analyzed by an immunoassay procedure, such as, for example, radioimmunoassay, fluorogenic immunoassay, magnetic immunoassay, enzyme-linked immunoassay, or surface plasmon resonance.

In some embodiments of these methods, the eluted free steroid, secosteroid, phytosteroid, oligopeptide, peptide, prodrug, drug, or metabolite thereof, derivatized or not, is analyzed by mass spectrometry. In some sub-embodiments, the free steroid, secosteroid, phytosteroid, oligopeptide, peptide, prodrug, drug, or metabolite thereof, derivatized or not, is subjected to separation by high pressure liquid chromatography (HPLC), or another suitable chromatographic method, prior to analysis by mass spectrometry.

In those embodiments of these methods where the eluted free steroid, secosteroid, phytosteroid, oligopeptide, peptide, prodrug, drug, or metabolite thereof is derivatized prior to analysis, it can be derivatized with Cookson type reagent or hydroxylamine type reagent prior to analysis. In certain sub-embodiments the derivatized eluted free steroid, secosteroid, phytosteroid, oligopeptide, peptide, prodrug, drug, or metabolite thereof is analyzed by mass spectrometry. In certain sub-embodiments, the mass spectrometry can be tandem mass spectrometry or triple quadrapole mass spectrometry.

In some embodiments of these methods, a defined amount of isotopically labeled steroid, secosteroid, phytosteroid, oligopeptide, peptide, prodrug, drug, or metabolite thereof is added to the sample before it is applied to the size exclusion chromatography matrix, or is added to the organic solvent used to elute the steroid or secosteroid from the size exclusion chromatography matrix. In some sub-embodiments, the eluted free steroid, secosteroid, phytosteroid, oligopeptide, peptide, prodrug, drug, or metabolite thereof and the eluted isotopically labeled steroid, secosteroid, phytosteroid, oligopeptide, peptide, prodrug, drug, or metabolite thereof are dried prior to further processing and analysis. In certain sub-embodiments a stream of heated air, nitrogen, or other inert gas is used to dry the eluted free steroid, secosteroid, phytosteroid, oligopeptide, peptide, prodrug, drug, or metabolite thereof and the eluted isotopically labeled steroid, secosteroid, phytosteroid, oligopeptide, peptide, prodrug, drug, or metabolite thereof.

In some sub-embodiments, the dried eluted free steroid, secosteroid, phytosteroid, oligopeptide, peptide, prodrug, drug, or metabolite thereof and eluted isotopically labeled steroid, secosteroid, phytosteroid, oligopeptide, peptide, prodrug, drug, or metabolite thereof are redissolved and simultaneously analyzed by mass spectrometry. In certain sub-embodiments the resdissolved eluted free steroid, secosteroid, phytosteroid, oligopeptide, peptide, prodrug, drug, or metabolite thereof and eluted isotopically labeled steroid, secosteroid, phytosteroid, oligopeptide, peptide, prodrug, drug, or metabolite thereof are simultaneously derivatized prior to analysis by mass spectrometry. In some sub-embodiments a Cookson-type reagent or a hydroxyamine type reagent is used for the derivatization prior to analysis by mass spectrometry.

In some embodiments of these methods the eluted free steroid, secosteroid, phytosteroid, oligopeptide, peptide, prodrug, drug, or metabolite thereof and eluted isotopically labeled steroid, secosteroid, phytosteroid, oligopeptide, peptide, prodrug, drug, whether derivatized or not, are subjected to separation by HPLC prior to mass spectrometry. In some sub-embodiments, tandem mass spectrometry or triple quadrapole mass spectrometry is employed for the analysis, and the in certain sub-embodiments the mass spectrometry is conducted in selected reaction monitoring mode or in multiple reaction monitoring mode.

Quantifying Free 25-Hydroxy Vitamin D3 and/or Free 25-Hydroxy Vitamin D2

The present disclosure also provides methods of determining the quantity of free 25-hydroxy vitamin D3 and/or free 25-hydroxy vitamin D2 in a sample, including processing the sample by the methods disclosed above, thereby separating free 25-hydroxy vitamin D3 and/or free 25-hydroxy vitamin D2 from protein-bound 25-hydroxy vitamin D3 and/or protein-bound 25-hydroxy vitamin D2, derivatizing the free 25-hydroxy vitamin D3 and/or the free 25-hydroxy vitamin D2; and detecting and quantifying derivatized free 25-hydroxy vitamin D3 and/or derivatized free 25-hydroxy vitamin D2 by mass spectrometry.

In some embodiments of such methods, free 25-hydroxy vitamin D3 and free 25-hydroxy vitamin D2 are separated, derivatized, detected and quantified simultaneously.

In some embodiments of such methods, the sample is serum or plasma, and if plasma, can be plasma prepared through the addition of EDTA or Heparin to whole blood.

In some embodiments of such methods, the sample is serum or plasma, and it is applied directly to the size exclusions matrix undiluted.

In some embodiments of such methods, the size exclusion matrix is washed with aqueous solution after the sample is applied to it.

In some embodiments of such methods, free 25-hydroxy vitamin D3 and/or free 25-hydroxy vitamin D2 are eluted from the size exclusion chromatography matrix with organic solvent, and in certain sub-embodiments the organic solvent used to elute free 25-hydroxy vitamin D3 and/or free 25-hydroxy vitamin D2 is a solvent in which free 25-hydroxy vitamin D3 and/or free 25-hydroxy vitamin D2 are soluble. In some sub-embodiments the organic solvent is an ether, for example, methyl tert-butyl ether or diisopropyl ether. In other sub-embodiments, the organic solvent is methanol. In still other sub-embodiments, the organic solvent is a mixture of an ether, such as methyl tert-butyl ether or diisopropyl ether, and methanol.

In some embodiments of such methods, isotopically-labeled 25-hydroxy vitamin D3 and/or isotopically-labeled 25-hydroxy vitamin D2 are added to the organic solvent used for elution. In such embodiments, the eluted free 25-hydroxy vitamin D3 and/or free 25-hydroxy vitamin D2 and isotopically-labeled 25-hydroxy vitamin D3 and/or isotopically-labeled 25-hydroxy vitamin D2, are derivatized with a Cookson-type reagent prior to detection and quantification by mass spectrometry. In certain sub-embodiments of such methods the Cookson-type reagent is selected from 4-[2-(3,4-dihydro-6,7-dimethoxy-4-methyl-3-oxo-2-quinoxalinyl)ethyl]-1,2,4-triazoline-3,5-dione (DMEQTAD); 4-[4-(6-methoxy-2-benzoxazolyl)phenyl]-1,2,4-triazoline-3,5-dione (MBOTAD); 4-methyl-1,2,4-triazoline-3,5-dione (MTAD); 4-phenyl-1,2,4-triazoline-3,5-dione (PTAD); or Amplifex™ diene reagent (3-[(E)-1-[4-(3,5-dioxo-1,2,4-triazol-4-yl)phenyl]ethylideneamino]oxypropyl-trimethylazanium)). In a particular sub-embodiments of such methods the Cookson-type reagent is Amplifex™ diene reagent (3-[(E)-1-[4-(3,5-dioxo-1,2,4-triazol-4-yl)phenyl]ethylideneamino]oxypropyl-trimethylazanium)).

In some embodiments of such methods, derivatized free 25-hydroxy vitamin D3 and/or derivatized free 25-hydroxy vitamin D2, and the derivatized isotopically-labeled 25-hydroxy vitamin D3 and/or derivatized isotopically-labeled 25-hydroxy vitamin D2, if present, are detected and quantified by mass spectrometry, and the mass spectrometry is tandem mass spectrometry or triple quadrapole mass spectrometry. In other embodiments of such methods, derivatized free 25-hydroxy vitamin D3 and/or derivatized free 25-hydroxy vitamin D2, and the derivatized isotopically-labeled 25-hydroxy vitamin D3 and/or derivatized isotopically-labeled 25-hydroxy vitamin D2 are subjected to HPLC separation before being detected and quantified by mass spectrometry, and the mass spectrometry is tandem mass spectrometry or triple quadrapole mass spectrometry. In certain sub-embodiments of these methods, the mass spectrometry is conducted in selected reaction monitoring mode or multiple reaction monitoring mode. In specific sub-embodiments of such methods, the detection and quantification by mass spectrometry involves the detection and quantification of one or more pair of parent (Q1) and fragment (Q3) molecular ions shown in the individual rows of the following transition table:

|  | Q1 Mass (Da) | Q3 Mass (Da) |
| --- | --- | --- |
| 25OHD3-1 | 732.5 | 673.5 |
| 25OHD3-2 | 732.5 | 217.1 |
| IS 25OHD3-1 | 735.5 | 676.5 |
| IS 25OHD3-2 | 735.5 | 217.1 |
| 25OHD2-1 | 744.5 | 685.5 |
| 25OHD2-2 | 744.5 | 217.1 |
| IS 25OHD2-1 | 747.5 | 688.5 |
| IS 25OHD2-2 | 747.5 | 217.1 | wherein "IS" indicates an isotopically labeled internal standard.

In those embodiments in which free 25-hydroxy vitamin D3 and/or free 25-hydroxy vitamin D2, and isotopically-labeled 25-hydroxy vitamin D3 and/or isotopically-labeled 25-hydroxy vitamin D2 are derivatized, the derivatization step enhances the sensitivity of detection, for example by about 10, about 50, about 100, about 500, or about 1000-fold.

In some embodiments of these methods, the limits of quantification of derivatized free 25-hydroxy vitamin D3 and/or derivatized free 25-hydroxy vitamin D2 are about 5 pg/mL.

In some embodiments of these methods, the limits of detection of derivatized free 25-hydroxy vitamin D3 and/or derivatized free 25-hydroxy vitamin D2 are about 2 pg/mL.

Diagnostic and Therapeutic Methods for Vitamin D Deficiency

The present disclosure also provides methods of identifying vitamin D deficiency in a patient including determining the quantity of free 25-hydroxy vitamin D3 and free 25-hydroxy vitamin D2 in a serum or plasma sample from said patient using the method of claim C1; and diagnosing said patient as having vitamin D deficiency when the concentration of free 25-hydroxy vitamin D3 and free 25-hydroxy vitamin D2 in the sample from said patient is below about 25 pg/mL.

In some embodiments of these methods, the sample is plasma prepared through the addition of EDTA or Heparin to whole blood.

The present disclosure also provides methods of treating vitamin D deficiency in a patient including determining the quantity of free 25-hydroxy vitamin D3 and free 25-hydroxy vitamin D2 in a serum or plasma sample from said patient using the method of claim C1; diagnosing said patient as having vitamin D deficiency when the concentration of free 25-hydroxy vitamin D3 and free 25-hydroxy vitamin D2 in the sample from said patient is found to be below about 25 pg/mL; and administering to said patient vitamin D supplementation therapy based upon the diagnosis.

In some embodiments of these methods, the sample is plasma prepared through the addition of EDTA or Heparin to whole blood.

Quantifying Free Testosterone

The present disclosure also provides methods of determining the quantity of free testosterone in a sample, including processing the sample by the method of claim 1, thereby separating free testosterone from protein-bound testosterone, derivatizing the free testosterone; and detecting and quantifying derivatized free testosterone by mass spectrometry.

In some embodiments of such methods, the sample is serum or plasma, and if plasma, can be plasma prepared through the addition of EDTA or Heparin to whole blood.

In certain sub-embodiments of such methods, the sample is serum or plasma, and it is applied directly to the size exclusions matrix undiluted.

In some embodiments of such methods, the size exclusion matrix is washed with aqueous wash solution after the sample is applied to it.

In some embodiments of such methods, free testosterone is eluted from the size exclusion chromatography matrix with organic solvent, and in certain sub-embodiments the organic solvent used to elute free testosterone is a solvent in which free testosterone is soluble. In some sub-embodiments the organic solvent is an ether, for example, methyl tert-butyl ether or diisopropyl ether. In other sub-embodiments, the organic solvent is methanol. In still other sub-embodiments, the organic solvent is a mixture of an ether, such as methyl tert-butyl ether or diisopropyl ether, and methanol.

In some embodiments of such methods, isotopically-labeled testosterone is added to the organic solvent used for elution. In such embodiments, the eluted free testosterone and isotopically-labeled testosterone, are derivatized with a hydroxylamine prior to detection and quantification by mass spectrometry.

In some embodiments of such methods, derivatized testosterone, and the derivatized isotopically-labeled testosterone, if present, are detected and quantified by mass spectrometry, and the mass spectrometry is tandem mass spectrometry or triple quadrapole mass spectrometry.

In other embodiments of such methods, derivatized free testosterone, and the derivatized isotopically-labeled testosterone are subjected to HPLC separation before being detected and quantified by mass spectrometry, and the mass spectrometry is tandem mass spectrometry or triple quadrapole mass spectrometry. In certain sub-embodiments of these methods, the mass spectrometry is conducted in selected reaction monitoring mode or multiple reaction monitoring mode. In specific sub-embodiments of such methods, the detection and quantification by mass spectrometry involves the detection and quantification of one or more pair of parent (Q1) and fragment (Q3) molecular ions shown in the individual rows of the following transition table:

|          | Q1 Mass (Da) | Q3 Mass (Da) |
|----------|--------------|--------------|
| Te 112   | 304.2        | 112.1        |
| Te 124   | 304.2        | 124.1        |
| IS Te 112| 307.2        | 112.1        |
| IS Te 124| 307.2        | 124.1        | wherein "IS" indicates an isotopically labeled internal standard.

In those embodiments in which free testosterone, and isotopically-labeled testosterone are derivatized, the derivatization step enhances the sensitivity of detection, for example by about 10, about 50, about 100, about 500, or about 1000 fold.

In some embodiments of these methods, the lower limits of quantification of derivatized testosterone is about 5 pg/mL.

In some embodiments of these methods, the upper limits of quantification of derivatized testosterone is about 2500 pg/mL.

Kits

The present disclosure also provides kits for practicing the methods disclosed above.

Such kits can include a size exclusion chromatography matrix with a molecular weight cut off sufficient to allow the free target analyte to permeate into the chromatography matrix and exclude the one or more target analyte binding proteins with bound target analyte; instructions for use; and optionally, one or more of the following:
- an aqueous wash solution,
- an organic solvent eluent, and
- a derivatization reagent.

In some embodiments, the size exclusion chromatography matrix comprises a polymer selected from macroporous cellulose, cross-linked dextran, cross-linked agarose, agarobiose, porous styrene divinylbenzene, cross-linked hydroxypropylated dextran, copolymers of acrylamide and N,N'-methylene-bis-acrylamide, copolymers of dextran and cross-linked agarose, and cross-linked allyl dextran and N,N'-methylene-bis-acrylamide, or combinations or derivatives of such polymers. In certain embodiments, the polymer of the size exclusion chromatography matrix is macroporous cellulose. In certain sub-embodiments of such kits, the polymer of the size exclusion chromatography matrix has a molecular weight cut off of about 1 kDa, about 2 kDa, about 5 kDa, about 7 kDa, about 10 kDA, about 15 kDa, about 20 kDa, about 30 kDa, about 40 kDa, or about 50 kDa.

In particular embodiments of such kits, the size exclusion chromatography matrix is structurally configured to be contained in a device designed to be eluted by gravity, where the aqueous sample, aqueous wash solution, and organic solvent eluent are passed through the size exclusion chromatography matrix by gravity. In other embodiments of such kits, the size exclusion chromatography matrix is structurally configured to be contained in a device designed to be placed in a centrifuge, where the aqueous sample, aqueous wash solution, and organic solvent eluent are forced through the size exclusion chromatography matrix by centrifugation. In still other embodiments of such kits, the size exclusion chromatography matrix is structurally configured to be contained in a device designed to be connected to negative or positive pressure source, where the aqueous sample, aqueous wash solution, and organic solvent eluent are pulled or pushed through the size exclusion chromatography matrix by negative or positive pressure, respectively.

Compositions

The present disclosure also provides compositions, including a size exclusion chromatography matrix composed of a size exclusion chromatography resin with a molecular weight cut off sufficient to allow a free target analyte to permeate into pores of the size exclusion chromatography resin and exclude protein-bound target analyte, an aqueous sample within the size exclusion chromatography matrix including a protein-bound target analyte bound to a target analyte binding protein within interstitial spaces of the size exclusion chromatography matrix and excluded from the pores, and a free target analyte permeated into and attached to the pores.

In some embodiments of such compositions, the size exclusion chromatography matrix comprises a porous size exclusion chromatography resin that further comprises spherical beads or globules.

In other embodiments of such compositions, the protein-bound target analyte has been removed from the size exclusion chromatography matrix. In certain sub-embodiments, the protein-bound target analyte has been removed from the size exclusion chromatography matrix, and the size exclusion chromatography matrix has been washed with an aqueous wash solution, but the free target analyte remains adhered to, and immobilized by, the size exclusion chromatography matrix.

It should be appreciated by those skilled in the art that the techniques disclosed in the examples which follow represent techniques discovered by the inventors to function well in the practice of the disclosed methods, and thus can be considered to constitute particular modes for its practice.

The following examples are provided for the purpose of illustration only. They are not intended to be limiting in any manner, and are not provided to specifically define or limit the scope of the present disclosure. Indeed, those of skill in the art should appreciate, in light of the present disclosure, that many changes can be made in the specific embodiments disclosed herein which will still obtain a like or similar result without departing from the spirit and scope of the disclosed methods.

EXAMPLES

Example 1—Measurement of Free 25-Hydroxy Vitamin D3 and Free 25-Hydroxy Vitamin D2 in Serum and Plasma by LC-MS/MS Utilizing Size Exclusion-Based Separation A. Introduction Similar to steroid and thyroid hormones, vitamin D is highly lipophilic and has protein carriers that help maintain its circulating stores in serum. The majority (i.e., 85-90%) of circulating vitamin D is in the form of 25-hydroxy vitamin D (25OHD), and is tightly bound to vitamin D binding protein (VDBP), an abundant circulating alpha-globulin produced by the liver. Approximately 10-15% of the 25OHD circulating in blood is bound to albumin. The binding constants of VDBP and albumin are 1000-fold different, with albumin being the weaker carrier [Bikle, D. D., et al., *J. Clin. Endocrinol. Metab.* 1986, 63(4), 954-959]. Less than 0.1% of circulating 25OHD is "free" (i.e., not protein bound) [Ibid.; Bouillon, R., et al. *J. Clin. Invest.* 67(3), 589-596]. Measurement of free 25OHD and free 1,25-dihydroxy vitamin D (1.25(OH)$_2$D) is technically difficult due to their low concentrations in plasma or serum, and due to their physicochemical behavior, specifically their propensity to nonspecifically adsorb, adhere, or otherwise bind to surfaces and substrates commonly contacted by biological fluid samples during sample handling, sample preparation, or sample analysis procedures [Bikle, D. D., et al., *J. Steroid Biochem. & Molec. Biol.,* 2017 October; 173:105-116]. The method described herein rapidly separates free from protein-bound 25OHD while simultaneously overcoming the problems associated with the physicochemical behavior of free 25OHD. The resulting free 25OHD is then derivatized to improve detection of the naturally low levels of free 25OHD observed in human serum or plasma.

Serum 25-hydroxy vitamin D (25OHD) is widely used as a biochemical marker to assess vitamin D storage. 25OHD is highly lipophilic and most of the 25OHD in serum is tightly bound by vitamin D binding protein (VDBP). A smaller fraction is bound by serum albumin. And an even smaller fraction exists in a non-protein-bound (i.e., unbound or "free") state. Similar to the mechanism of several other hormones, it has been demonstrated that the majority of cells in the human body respond to the free form of 25OHD, rather than total 25OHD. Consequently, measurement of free 25OHD is likely more relevant than total 25OHD for assessment vitamin D sufficiency, and pathologies resulting from vitamin D insufficiency [Bikle, D. D., et al., *J. Steroid Biochem. & Molec. Biol.,* 2017 October; 173:105-116]. Two methods for determining free 25OHD concentrations in serum or plasma currently exist; an ELISA (Future Diagnostics, the Netherlands), and a calculation-based method utilizing measured serum concentrations of total 25OHD, VDBP and albumin, and the corresponding binding constants of the two binding proteins. Both of these methods are believed to have low accuracy and precision.

Described below is an example method for rapidly separating free 25OHD from bound 25OHD using size exclusion media, followed by a liquid chromatography, tandem mass spectrometry (LC-MS/MS) method for the measurement of free 25OHD.

B. Calibration

Calibration is performed using standards with a concentration 40, 100, 200 and 300 pg/mL of 25-hydroxyvitamin D2 and 25-hydroxyvitamin D3. Calibration standards are prepared and analyzed with every batch of samples.

C. Quality Controls

Negative control: Negative Control for the assay is HEPES buffer.

Control level I, 10-40 pg/mL of Free 25-Hydroxyvitamin D2 and D3: prepared pool of discarded patient serum samples.

Control Level II, 50-100 pg/mL of Free 25-Hydroxyvitamin D2 and D3: prepared pool of discarded patient serum samples.

Control Level III, 120-200 pg/mL of Free 25-Hydroxyvitamin D2 and D3: prepared pool of discarded patient serum samples.

D. Extraction of Free 25-Hydroxy Vitamin D

1. Set tubes with patient samples and controls on a rocking mixer and rock tubes for 2 hours at room temperature; remove a 96-well Zeba™ desalting plate (Part #89807/89808; ThermoScientific, Waltham, Mass.) from refrigerator and keep at room temperature for 2 hours. Prepare and print layout map of the 96-well plate with sample IDs listed in corresponding wells of the map (Table 1).

TABLE 1

Example of the layout map of 96-well plate.

| | 1 | 2 | 3 | 4 | 5 | 6 | 7 | 8 | 9 | 10 | 11 | 12 |
|---|---|---|---|---|---|---|---|---|---|---|---|---|
| A | Control A1 | Sp 5 | Sp 13 | Sp 21 | Sp 29 | Sp 37 | | Sp 45 | Cal Std 1 | | | |
| B | Control B1 | Sp 6 | Sp 14 | Sp 22 | Sp 30 | Sp 38 | | Sp 46 | Cal Std 2 | | | |
| C | Control C1 | Sp 7 | Sp 15 | Sp 23 | Sp 31 | Sp 39 | | Sp 47 | Cal Std 3 | | | |
| D | Negative Control | Sp 8 | Sp 16 | Sp 24 | Sp 32 | Sp 40 | | Sp 48 | Cal Std 4 | | | |

TABLE 1-continued

Example of the layout map of 96-well plate.

| | 1 | 2 | 3 | 4 | 5 | 6 | 7 | 8 | 9 | 10 | 11 | 12 |
|---|---|---|---|---|---|---|---|---|---|---|---|---|
| E | Sp 1 | | Sp 9 | Sp 17 | Sp 25 | Sp 33 | Sp 41 | Sp 49 | Dbl Neg | | | |
| F | Sp 2 | | Sp 10 | Sp 18 | Sp 26 | Sp 34 | Sp 42 | Control A2 | | | | |
| G | Sp 3 | | Sp 11 | Sp 19 | Sp 27 | Sp 35 | Sp 43 | Control B2 | | | | |
| H | Sp 4 | | Sp 12 | Sp 20 | Sp 28 | Sp 36 | Sp 44 | Control C2 | | | | |

Sp = sample;
Cal Std = calibration standard;
Dbl Neg = double negative control;
empty cells = unused wells.

2. Centrifuge the tubes containing the controls at 10,000 g for 2 min. Aliquot 150 µL of samples and controls into the wells of the 96-well plate. Add 150 µL of HEPES buffer in the well corresponding to the Negative control. Seal the 96-well plate with sealing film, and centrifuge the plate at 2,000 g for 2 minutes.

3. Remove sealing foil from the bottom and the top of the wells of Zeba™ desalting plate. Set the 96-well wash collection plate in the plate holder, and set the 96-well desalting plate on top of the wash collection plate.

4. Prepare desalting plate. Centrifuge the assembly at 1000 g for 4 min in order to remove the storage buffer from the wells of the plate.

5. Prepare the 96-well positive pressure processor, and process the 96-well desalting plate as follows:
 a) Using an 8-channel pipet add 250 µL of water in the wells of the desalting plate.
 b) Set 96-well desalting plate on top of a deep 24-well waste collection plate.
 c) Activate the compression mechanism using two toggle switches to lower the manifold
 d) Apply pressure (7+/−2 psi) for 1 min.
 e) Depress the top portion of both toggle switches until the manifold is all the way up and has stopped moving.
 f) Perform additional two washes of the wells by repeating steps a-e.

6. Set the 96-well desalting plate on top of the wash collection plate, centrifuge the assembly at 1000 g for 4 min. Discard filtrate from the collection plate.

7. Using 8 channel pipet quantitatively transfer 100 µL of the controls and patient samples from the initial 96-well plate into the wells of the desalting plate.

8. After the last row of samples is added to the wells of the desalting plate start timer and hold the desalting plate on the bench for 10 min.

9. Centrifuge the assembly (96-well desalting plate/96-well wash collection plate in plate holder) at 1000 g for 4 min. Discard filtrate from the collection plate in a biohazard waste container.

10. Using a 96-well positive pressure processor perform 3 consecutive washes of the wells of the desalting plate with 2504, of water (as described in step 5, above).

11. Prepare the working combined internal standard (IS) ($^{13}C_3$-25-hydroxy vitamin D2, 0.05 pg/µL and $d_3$-25-hydroxy vitamin D3, 0.05 pg/µL) in diisopropyl ether (DIPE).

12. Centrifuge assembly at 2,000 g for 4 min.

13. Label elution plate.

14. Set 96-well elution collection plate in the plate holder, set 96-well desalting plate on top of the elution plate.

15. Using 8-channel pipet, add 200 µL of DIPE/IS working solution into the wells of the desalting plate. After the solvent is added to all wells, start timer and hold the desalting plate on bench for 3 min.

16. Centrifuge the assembly at 2000 g for 4 min.

17. Prepare calibration standards of 25OH vitamin D2 and 25OH vitamin D3 (Table 2). Quantitatively add 200 µL of the working combined internal standard in the wells of the elution plate corresponding to the calibration standards.

TABLE 2

Preparation of the calibration standards.

| | Concentration, pg/mL | Working calibration standard, µL | Working internal standard (prepared in DIPE solvent; see step 11 of this procedure), µL |
|---|---|---|---|
| Calibrator 1 | 40 | 2 | 200 |
| Calibrator 2 | 100 | 5 | 200 |
| Calibrator 3 | 200 | 10 | 200 |
| Calibrator 4 | 300 | 15 | 200 |

18. Evaporate solvent from the plate.

E. Derivatization

1. Prepare a working solution of Amplifex™ Diene derivatizing reagent (Part #5037804; SCIEX, Redwood City, Calif.) in acetonitrile. In a new LoBind microcentrifuge tube aliquot 14 parts of acetonitrile and 1 part of the Stock derivatizing reagent, Amplifex™ Diene.

2. Add 30 µL of the working solution of the diluted Amplifex™ Diene derivatizing reagent in the wells of the elution plate corresponding to the samples, controls and calibrators. Seal wells of the plate with sealing film.

3. Set the plate on the platform of a Thermomixer and shake the plate at 500 rpm for 60 min at 20° C.

4. Peel off and discard the sealing film, add 40 µL of water in the wells of the plate.

5. Seal wells of the plate with sealing film. Set plate on the platform of a Thermomixer and shake for 2 min at 20° C.; centrifuge plate for 1 min at 4000 g.

6. Analyze the samples.

F. Instrumental Analysis

LC separation:

HPLC column for $1^{st}$ dimensions separation (FIG. 2): HPLC column Zorbax Eclipse XDB-CN, 2.1×50, 5 µm (part #89040-838, Agilent Technologies, Santa Clara, Calif.).

HPLC column for $2^{nd}$ dimensions separation (Poroshell 120 SB-C18 50×3 2.7 µm particles (Agilent Technologies, part #689975-302, Santa Clara, Calif.).

Mobile phase for $1^{st}$ and $2^{nd}$ columns: bottle A—water with 0.1% formic acid, bottle B—methanol (Optima) with 0.1% formic acid. Store at room temperature, stable for 3 days.

HPLC pumps gradient is shown in Table 3.

Autosampler wash solvents. Wash 1:20% methanol, 80% water, 1% formic acid. Wash 2:80% methanol, 20% water 0.1% trifluroacetic acid.

Figure 1B:
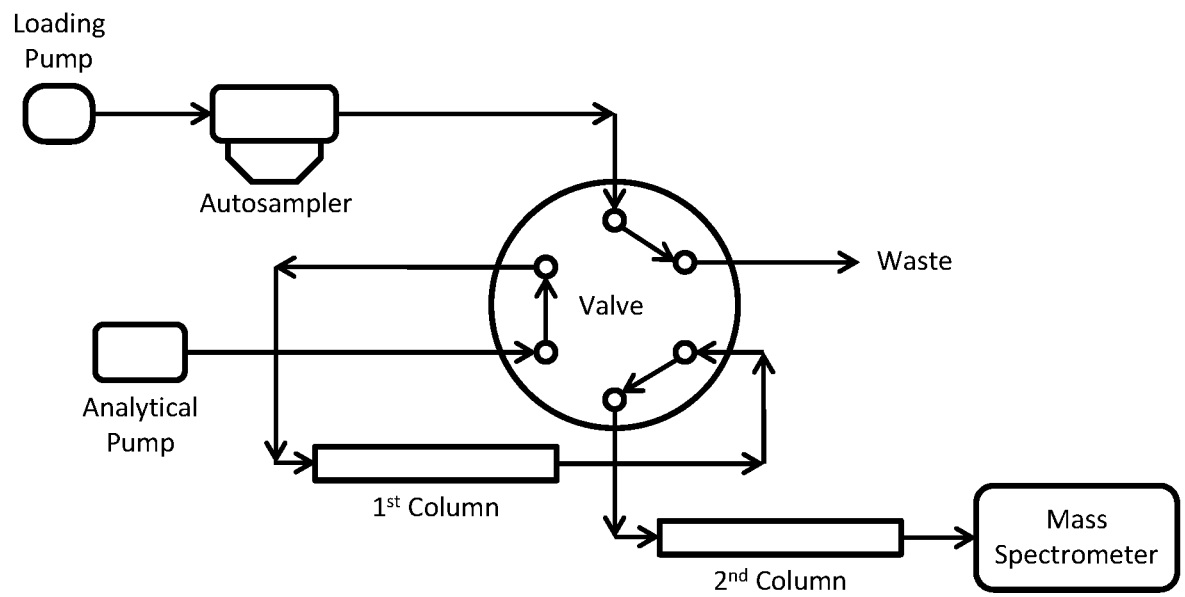
FIG. 1B schematically depicts one example setup for a chromatographic separation and detection method that can be employed in Examples 1 and 2, with the switching valve configured for elution and separation of the bound analyte according to one example embodiment.

HPLC and Mass Spectrometer:

FIG. 1A schematically depicts one example setup for the chromatographic separation and detection of target analytes with the switching valve configuration for loading the sample onto the $1^{st}$ dimension (first) column; and FIG. 1B schematically depicts the same example setup for the chromatographic separation and detection of target analytes shown in FIG. 1A, with the switching valve configuration for elution of the bound material from the $1^{st}$ dimension (first) column and separating that eluted bound material on the $2^{nd}$ dimension (second) column.

TABLE 3

HPLC method

| Step | Total Time (min) | Flow Rate (µl/min) | A (%) | B (%) |
|---|---|---|---|---|
| Pump Model: Agilent 1260 Binary Pump | | | | |
| 0 | 0.1 | 700 | 80 | 20 |
| 1 | 0.2 | 700 | 80 | 20 |
| 2 | 1.2 | 700 | 25 | 75 |
| 3 | 2.6 | 700 | 25 | 75 |
| 4 | 2.7 | 700 | 3 | 97 |
| 5 | 4.1 | 700 | 3 | 97 |
| 6 | 4.2 | 700 | 80 | 20 |
| 7 | 6.0 | 700 | 80 | 20 |
| Pump Model: Agilent 1290 Binary Pump | | | | |
| 0 | 0.1 | 1000 | 60 | 40 |
| 1 | 1.5 | 1000 | 60 | 40 |
| 2 | 3.2 | 1000 | 30 | 70 |
| 3 | 4.6 | 1000 | 30 | 70 |
| 4 | 4.7 | 1000 | 3 | 97 |
| 5 | 5.9 | 1000 | 3 | 97 |
| 6 | 6.0 | 1000 | 60 | 40 |

HPLC and Mass Spectrometer Run Parameters:

1. HPLC columns temperature: 45° C.

2. Injection volume: 10 µL.

3. Switching valve in the column oven: Direct effluent from the 1st column to waste before 1.6 and after 2.2 min; transfer effluent from the 1st to 2nd HPLC column between 1.6 and 2.2 min.

4. Diverter valve: Direct effluent to waste before 3.0 and after 4.5 min; direct effluent from the HPLC column in the ion source 3.0 to 4.5 min.

5. Ion source settings are listed in Table 4.

6. MRM transitions monitored in the method are listed in Table 5.

7. Mass spectrometer voltages optimized for maximum sensitivity; collision energy (CE) is compound-dependent (Table 4). Mass analyzers (Q1 and Q3) tuned for unit resolution (0.7 amu at 50% height).

TABLE 4

Mass Spectrometer conditions

| | |
|---|---|
| CUR: | 35 |
| TEM: | 650 |
| GS1: | 90 |
| GS2: | 90 |
| CAD: | High |
| IS: | 5500 |
| DP | 40 |
| EP | 5 |
| CXP | 20 |

TABLE 5

Mass transitions and mass transition-specific parameters

| Q1 Mass (Da) | Q3 Mass (Da) | Dwell (msec) | Collision energy, V | ID |
|---|---|---|---|---|
| 732.5 | 673.5 | 40 | 42 | 25OHD3 673 |
| 732.5 | 217.1 | 40 | 65 | 25OHD3 217 |
| 735.5 | 676.5 | 40 | 42 | IS 25OHD3 676 |
| 735.5 | 217.1 | 40 | 65 | IS 25OHD3 217 |
| 744.5 | 685.5 | 40 | 42 | 25OHD2 685 |
| 744.5 | 217.1 | 40 | 65 | 25OHD2 217 |
| 747.5 | 688.5 | 40 | 42 | IS 25OHD2 688 |
| 747.5 | 217.1 | 40 | 65 | IS 25OHD2 217 |

G. Quantitation

Concentration of the analytes in the samples is calculated using peak area ratios and the calibration curves generated with every batch of samples. Calibration curves are linear; concentrations of 25OH vitamin D2 and 25OH vitamin D3 are determined from the quantitative mass transitions of the analytes and the internal standards. Specificity of the analysis is evaluated using ratio of peak areas of the primary and the secondary mass transitions of the analytes and the internal standards.

H. Discussion & Results

The lower limits of quantification and the upper limits of linearity for the assay for 25OHD2 and 25OHD3 were 5 pg/mL and 3000 pg/mL, respectively. Total imprecision of triplicate measurements in serum samples over five days was <18%. Reasonably good correlation ($r^2=0.787$, n=62) was observed with the commercially-available ELISA, although the concentrations measured by ELISA were, on average, 6.2 times lower than the concentrations measured by the LC-MS/MS method disclosed. One likely explanation for the lower measured concentrations is non-specific, and irreversible binding of free 25OHD to the labware used to conduct the ELISA.

Using the disclosed LC-MS/MS method, reference intervals for 25OHD3 in serum samples from self-reported healthy adults (n=230) were established, since measurable concentrations of free 25OHD3 were observed in all samples analyzed. Moreover, there was a better association between parathyroid hormone (PTH) levels with measured concentrations of free 25OHD (p=0.0024) than with total 25OHD (p=0.082), suggesting that free 25OHD levels are more reflective of health, than are total 25OHD levels.

The data obtained with the assay for free 25OHD described above, suggest that this assay is specific to free 25OHD, and support the conclusion that this assay's performance characteristics are acceptable for use in clinical diagnostic applications. Moreover, the sensitivity of the method is sufficient for quantitative measurements of free 25OHD in serum and plasma samples at concentrations expected in both health and pathology.

Example 2—Measurement of Free Testosterone in Serum and Plasma by LC-MS/MS Utilizing Size Exclusion Based Separation A. Introduction Testosterone (Te) is a steroid hormone primarily secreted by testes in males and by ovaries in females; small amounts of Te are produced by the adrenal glands. In men Te is typically measured to diagnose erectile dysfunction, infertility, decreased muscle or skeletal mass, decreased body hair, low energy, fatigue, changes in mood, decreased cognitive function; in women Te is measured to diagnose hyperandrogenism, hirsutism and polycystic ovarian disease. The majority of Te circulates in blood bound to proteins, with a small fraction (1-3%) present in an unbound, free, form. Approximately 60-70%, of the protein bound Te is strongly bound to sex hormone-binding globulin (SHBG) and the remainder is weakly bound to albumin. Measurement of the free (unbound fraction) of serum Te (free Te) is used for determining concentration of the physiologically bioactive hormone. Similar to the mechanism of action of several other hormones, it has been demonstrated that the majority of cells in the human body respond to free Te, rather than total Te. Consequently, measurement of free Te was shown to be more relevant that total Te in conditions associated with Te excess or insufficiency.

Two of the most commonly used methods for determining free Te concentrations in serum or plasma are dialyses based separation of free Te, followed by the measurement of the separated fraction using mass spectrometry based methods, and a calculation-based method utilizing measured serum concentrations of total Te, SHBG and albumin, along with the corresponding binding constants for the two binding proteins.

Described below is a method for separating free Te from bound Te using size exclusion media, followed by a liquid chromatography, tandem mass spectrometry (LC-MS/MS) method for the measurement of the free Te.

B. Calibration

Calibration is performed using standards with concentration 5, 50, 500 and 2500 pg/mL of free Te. Working Internal Standard (d3-Te) is prepared at concentration of 5 pg/μL.

Calibration standards are prepared and analyzed with every batch of samples.

C. Quality Controls

Negative control: Negative Control for the assay is HEPES buffer.

Control level 1. Pool of patient serum specimens containing ~5 pg/mL of free Te: prepared pool of discarded patient serum samples.

Control level 2. Pool of patient serum specimens containing ~60 pg/mL of free Te: prepared pool of discarded patient serum samples.

Control level 3. Pool of patient serum specimens containing ~200 pg/mL of free Te: prepared pool of discarded patient serum samples.

D. Extraction of Free Te

1. Set tubes with patient samples and controls on a rocking mixer and rock tubes for 2 hours at room temperature; remove Zeba plate from refrigerator and keep at room temperature for 2 hours. Prepare and print a layout map of the 96-well plate with sample IDs listed in corresponding wells of the map (Table 6).

TABLE 6

Example of the layout map of 96-well plate.

|   | 1 | 2 | 3 | 4 | 5 | 6 | 7 | 8 | 9 | 10 | 11 | 12 |
|---|---|---|---|---|---|---|---|---|---|----|----|----|
| A | Control A1 | Sp 5 | Sp 13 | Sp 21 | Sp 29 | Sp 37 | Sp 45 | Cal Std 1 | | | | |
| B | Control B1 | Sp 6 | Sp 14 | Sp 22 | Sp 30 | Sp 38 | Sp 46 | Cal Std 2 | | | | |
| C | Control C1 | Sp 7 | Sp 15 | Sp 23 | Sp 31 | Sp 39 | Sp 47 | Cal Std 3 | | | | |
| D | Negative Control | Sp 8 | Sp 16 | Sp 24 | Sp 32 | Sp 40 | Sp 48 | Cal Std 4 | | | | |
| E | Sp 1 | Sp 9 | Sp 17 | Sp 25 | Sp 33 | Sp 41 | Sp 49 | Dbl Neg | | | | |
| F | Sp 2 | Sp 10 | Sp 18 | Sp 26 | Sp 34 | Sp 42 | Control A2 | | | | | |
| G | Sp 3 | Sp 11 | Sp 19 | Sp 27 | Sp 35 | Sp 43 | Control B2 | | | | | |
| H | Sp 4 | Sp 12 | Sp 20 | Sp 28 | Sp 36 | Sp 44 | Control C2 | | | | | |

Sp = sample;
Cal Std = calibration standard;
Dbl Neg = double negative control;
empty cells = unused wells.

2. Centrifuge tubes with the controls at 10,000 g for 2 min. Aliquot 150 μL of samples and controls in the wells of the 96-well plate. Add 150 μL of HEPES buffer in the well corresponding to the Negative control. Seal the 96-well plate with sealing film, centrifuge the plate at 2,000 g for 2 minutes.

3. Remove sealing foil from the bottom and the top of the wells of Zeba™ desalting plate. Set a 96-well wash collection plate in plate holder, and set the 96-well desalting plate on top of the wash collection plate.

4. Prepare desalting plate. Centrifuge the assembly at 1000 g for 4 min in order to remove the storage buffer from the wells of the plate.

5. Prepare a 96-well positive pressure processor, and process the 96-well desalting plate as follows:
   a) Using 8-channel pipet add in the wells of the desalting plate 250 μL of water.
   b) Set 96-well desalting plate on top of a deep 24-well waste collection plate.
   c) Activate the compression mechanism using two toggle switches to lower the manifold
   d) Apply pressure (7+/−2 psi) for 1 min.
   e) Depress the top portion of both toggle switches until the manifold is all the way up and has stopped moving.
   f) Perform additional two washes of the wells by repeating steps a-e.

6. Set the 96-well desalting plate on top of the wash collection plate, centrifuge the assembly at 1000 g for 4 min. Discard filtrate from the collection plate.

7. Using an 8-channel pipet quantitatively transfer 100 μL of the controls and patient samples from the initial 96-well plate into the wells of the desalting plate.

8. After the last row of samples is added to the wells of the desalting plate start a timer and hold the desalting plate on bench for 10 min.

9. Centrifuge the assembly (96-well desalting plate/96-well wash collection plate in plate holder) at 1000 g for 4 min. Discard the filtrate from the collection plate in a biohazard waste container.

10. Using the 96-well positive pressure processor perform 3 consecutive washes of the wells of the desalting plate with 250 μL of water (as described in step 5).

11. Prepare working combined internal standard ($d_3$-Te, 0.5 pg/μL in diisopropyl ether (DIPE)).

12. Centrifuge assembly at 2,000 g for 4 min.

13. Label the elution plate.

14. Set the 96-well elution collection plate in the plate holder, set the 96-well desalting plate on top of the elution plate.

15. Using an 8-channel pipet, add 200 μL of DIPE/IS working solution into the wells of the desalting plate. After the solvent is added to all wells, start timer and hold the desalting plate on bench for 3 min.

16. Centrifuge the assembly at 2000 g for 4 min.

17. Prepare calibration standards of free Te (Table 7). Quantitatively add in the wells corresponding to the calibration standards 200 μL of the working combined internal standard.

TABLE 7

Preparation of the calibration standards.

|  | Concentration, pg/mL | Working internal standard (prepared in DIPE solvent; see step 11 of this procedure), μL |
|---|---|---|
| Calibrator 1 | 5 | 200 |
| Calibrator 2 | 50 | 200 |
| Calibrator 3 | 500 | 200 |
| Calibrator 4 | 2500 | 200 |

18. Evaporate solvent from the plate.

E. Derivatization

1. Prepare solution of derivatizing reagent (5% Hydroxylamine hydrochloride in 30% methanol/70% water).

2. Add 75 μL of the hydroxylamine derivatizing reagent in wells of the elution plate corresponding to the samples, controls and calibrators. Seal the wells of the plate with sealing film.

3. Set plate on platform of a Thermomixer and shake the plate at 500 rpm for 30 min at 60° C.

4. Peel off and discard the sealing film, add 75 μL of water in the wells of the plate.

5. Seal wells of the plate with sealing film. Set the plate on platform of a Thermomixer and shake for 2 min at 20° C.

6. Analyze the samples.

F. Instrumental Analysis LC Separation:

HPLC column for $1^{st}$ dimensions separation (FIG. 2): HPLC SecurityGuard™ cartridge holder with two C6 cartridges (Phenomenex, CA).

HPLC column for $2^{nd}$ dimensions separation: Kinetics C18, 50×21, 2.6 μm particles (Phenomenex, CA).

Mobile phase for 1st column: bottle A—10 mM formic acid in water, bottle B—10 mM formic acid in methanol.

Mobile phase for 2nd column: bottle A—10 mM formic acid in water, bottle B—10 mM formic acid in acetonitrile.

HPLC pumps gradient is shown in Table 8.

HPLC and Mass Spectrometer:

FIG. 1A schematically depicts one example setup for the chromatographic separation and detection of target analytes with the switching valve configuration for loading the sample onto the $1^{st}$ dimension (first) column; and FIG. 1B schematically depicts the same example setup for the chromatographic separation and detection of target analytes shown in FIG. 1A, with the switching valve configuration for elution of the bound material from the $1^{st}$ dimension (first) column and separating that eluted bound material on the $2^{nd}$ dimension (second) column.

TABLE 8

HPLC method

| Step | Total Time (min) | Flow Rate (μl/min) | A (%) | B (%) |
|---|---|---|---|---|
| Pump Model: Agilent Technologies Series 1260 Binary Pump | | | | |
| 0 | 0.0 | 750 | 85 | 15 |
| 1 | 1.5 | 750 | 3 | 97 |
| 2 | 2.8 | 750 | 3 | 97 |
| 3 | 2.9 | 750 | 85 | 15 |
| 4 | 3.9 | 750 | 85 | 15 |
| Pump Model: Agilent Technologies Series 1290 Binary Pump | | | | |
| 0 | 0.0 | 600 | 70 | 30 |
| 1 | 0.5 | 600 | 70 | 30 |
| 2 | 2.8 | 600 | 33 | 67 |
| 3 | 2.9 | 600 | 3 | 97 |
| 4 | 3.9 | 600 | 3 | 97 |

HPLC and Mass Spectrometer Run Parameters:

1. HPLC columns temperature: 30° C.

2. Injection volume: 40 μL.

3. Switching valve in the column oven: direct effluent from the 1st column to waste before 0.5 and after 1.3 min; transfer effluent from the 1st to 2nd HPLC column between 0.5 and 1.3 min.

4. Diverter valve: direct effluent from the HPLC column in the ion source 1.0 to 3.7 min.

Mass Spectrometer: AB6500 (AB SCIEX).

Ion source settings are listed in Table 9.

TABLE 9

Mass Spectrometer conditions.

| CUR: | 35 |
|---|---|
| TEM: | 600 |
| GS1: | 80 |
| GS2: | 80 |
| CAD: | High |
| IS: | 4500 |
| DP | 90 |
| EP | 10 |
| CE | 38 |
| CXP | 9 |

MRM transitions monitored in the method are listed in Table 10.

Mass spectrometer voltages optimized for maximum sensitivity; collision energy (CE) is compound-dependent (Table 9). Mass analyzers (Q1 and Q3) tuned for unit resolution.

TABLE 10

Mass transitions and mass transition-specific parameters.

| Q1 Mass (Da) | Q3 Mass (Da) | Dwell (msec) | Collision energy, V | ID |
|---|---|---|---|---|
| 304.2 | 112.1 | 70 | 42 | Te 112 |
| 304.2 | 124.1 | 70 | 65 | Te 124 |
| 307.2 | 112.1 | 70 | 42 | IS Te 112 |
| 307.2 | 124.1 | 70 | 65 | IS Te 124 |

G. Quantitation

The concentration of the analytes in the samples is calculated using peak area ratios and the calibration curves generated with every batch of samples. Calibration curves are linear; concentrations of free Te are determined from the quantitative mass transitions of the analytes and the internal standards. Specificity of the analysis is evaluated using ratio of peak areas of the primary and the secondary mass transitions of the analytes and the internal standards.

H. Discussion & Results

The lower limits of quantification and the upper limits of linearity for the assay for free Te were 5 and 2500 pg/mL, respectively.

Example 3—Measurement of Free Dihydrotestosterone (DHT) in Serum and Plasma by LC-MS/MS Utilizing Size Exclusion Based Separation It is believed that the methods disclosed herein can separate free from protein-bound DHT. Preliminary experiments have been conducted that suggest the disclosed methods will also work for this hydrophobic small-molecule analyte. Additional experiments are underway to confirm that these disclosed methods will facilitate the detection and quantification of the free form of this important androgen steroid.

All publications and patent applications mentioned in this specification are indicative of the level of those skilled in the art to which this disclosure pertains. All such publications and patent applications are herein incorporated by reference to the same extent as if each individual publication or patent application was specifically and individually indicated to be incorporated by reference. The mere mentioning of such publications and patent applications does not necessarily constitute an admission that they are prior art to the instant application.

Although the foregoing disclosure has been described in some detail by way of illustration and example for purposes of clarity of understanding, it will be apparent that certain changes and modifications may be practiced within the scope of the appended claims.

What is claimed is:

1. A method of separating free target analyte from protein-bound target analyte, comprising:
    obtaining an aqueous sample that contains a target analyte in a free form (free target analyte) and the target analyte in a protein-bound form (protein-bound target analyte) in which the target analyte is bound to a target analyte binding protein;
    passing the aqueous sample through a size exclusion chromatography matrix with a molecular weight cut off sufficient to allow the free target analyte to permeate into pores of the size exclusion chromatography matrix and exclude the protein-bound target analyte, whereupon the free target analyte adheres to and is immobilized by the size exclusion chromatography matrix and the protein-bound target analyte does not adhere to by the size exclusion chromatography matrix;
    separating the free target analyte from the protein-bound analyte by removing the protein-bound target analyte from the size exclusion chromatography matrix; and
    eluting the free target analyte from the size exclusion chromatography matrix with an organic solvent.

2. The method of claim 1, wherein the protein-bound target analyte is bound by more than one target analyte binding protein.

3. The method of claim 1, further comprising washing the size exclusion chromatography matrix with an aqueous wash solution before eluting the free target analyte from the size exclusion chromatography matrix with the organic solvent.

4. The method of claim 1, wherein the target analyte is a vitamin or a metabolite thereof.

5. The method of claim 4, where the target analyte includes a vitamin selected from the group consisting of 25-hydroxy vitamin D3, 25-hydroxy vitamin D2, and a combination thereof.

6. The method of claim 1, wherein the target analyte is a steroid, a secosteroid, a phytosteroid, or a metabolite thereof.

7. The method of claim 6, where the target analyte is an estrogen, an androgen, or a metabolite thereof.

8. The method of claim 7, wherein the androgen is testosterone and/or dihydrotestosterone.

9. The method of claim 1, wherein the target analyte is a prodrug, drug, or metabolite thereof.

10. The method of claim 9 where the drug is phenytoin, digoxin, carbamazepine, valproic acid, disopyramide, paclitaxel, mycophenolic acid, mycophenolate mofetil, lidocaine, xylocaine, lignocaine, or a metabolite thereof.

11. The method of claim 1, wherein the target analyte is an oligopeptide or a peptide.

12. The method of claim 1, wherein the method further comprises simultaneously separating free additional analytes from corresponding bound additional analytes.

13. The method of claim 12, wherein the free additional analytes are selected from steroids, secosteroids, phytosteroids, oligopeptides or peptides, prodrugs, drugs, or metabolites thereof, and are separated simultaneously with the free target analyte.

14. The method of claim 1, wherein the size exclusion chromatography matrix comprises a polymer selected from macroporous cellulose, cross-linked dextran polymer, cross-linked agarose, polymers of agarobiose, porous styrene divinylbenzene, cross-linked hydroxypropylated dextran, copolymers of acrylamide and N,N'-methylene-bis-acrylamide, copolymers of dextran and cross-linked agarose, or cross-linked allyl dextran and N,N'-methylene-bis-acrylamide, including combinations or derivatives thereof.

15. The method of claim 14, wherein the polymer of the size exclusion chromatography matrix is macroporous cellulose.

16. The method of claim 14, wherein the polymer of the size exclusion chromatography matrix has a molecular weight cut off of about 1 kDa, about 2 kDa, about 5 kDa, about 7 kDa, about 10 kDA, about 15 kDa, about 20 kDa, about 30 kDa, about 40 kDa, or about 50 kDa.

17. The method of claim 1, wherein the target analyte is soluble in the organic solvent used to elute the free target analyte from the size exclusion chromatography matrix.

18. The method of claim 17, wherein the organic solvent used to elute the free target analyte from the size exclusion chromatography matrix is methyl tert-butyl ether, diisopropyl ether, methanol, or combinations thereof.

19. The method of claim 1, wherein the target analyte is 25-hydroxy vitamin D3 and/or 25-hydroxy vitamin D2, the aqueous sample is human plasma or serum, the size exclusion chromatography matrix is macroporous cellulose, and the organic solvent is diisopropyl ether.

20. The method of claim 1, wherein the target analyte is testosterone, the aqueous sample is human plasma or serum, the size exclusion chromatography matrix is macroporous cellulose, and the organic solvent is diisopropyl ether.

* * * * *